(12) United States Patent
Gelber

(10) Patent No.: US 7,183,389 B2
(45) Date of Patent: Feb. 27, 2007

(54) MONOCLONAL ANTIBODIES AND CELL SURFACE ANTIGENS FOR THE DETECTION AND TREATMENT OF SMALL CELL LUNG CANCER (SCLC)

(75) Inventor: Cohava Gelber, Hartsdale, NY (US)

(73) Assignee: Molecular Discoveries, LLC, New York, NY (US)

( * ) Notice: Subject to any disclaimer, the term of this patent is extended or adjusted under 35 U.S.C. 154(b) by 602 days.

(21) Appl. No.: 10/015,728

(22) Filed: Nov. 1, 2001

(65) Prior Publication Data

US 2002/0137109 A1    Sep. 26, 2002

Related U.S. Application Data

(60) Provisional application No. 60/245,340, filed on Nov. 2, 2000.

(51) Int. Cl.
*C07K 16/00* (2006.01)
(52) U.S. Cl. .................... 530/388.1; 435/326
(58) Field of Classification Search ............. 424/141.1; 435/326, 330; 530/388.8
See application file for complete search history.

(56) References Cited

U.S. PATENT DOCUMENTS

| 4,585,742 A | 4/1986 | Bernal |
| 5,614,373 A | 3/1997 | Stahel ................. 435/7.23 |
| 5,665,864 A | 9/1997 | Quaranta et al. |
| 6,162,616 A | 12/2000 | Shyjan ................. 435/69.1 |

FOREIGN PATENT DOCUMENTS

WO    WO 98/35985    8/1998

OTHER PUBLICATIONS

Krueger et al., (2003, Cancer Immunol Inmmunother vol. 52, pp. 367-377).*
Freshney (Culture of Animal Cells, A Manual of Basic Technique, Alan R. Liss, Inc., 1983, New York, p. 4).*
Dermer (Bio/Technology, 1994, 12:320).*
Voet et al., (1990, Biochemistry, John Wiley & Sons, p. 98, and 99 only).*
Ward, ES (1992, Antibody Engineering, W. H. Freeman and Company, Car. A. K. Borrebaeck, ed, pp. 122-123 only).*
Rose et al., 1994, "A novel antigen defined by monoclonal antibody CR101 is associated with small cell lung carcinoma" *Hybridoma* 13(3):221-227.
Pettijohn, D. E. et al., "Glycoproteins Distinguishing Non-Small from Small Cell Human Lung Carcinoma Recognized by Monoclonal Antibody 43-9F," *Cancer Research*, 47:1161-1169, Feb. 15, 1987.
Waibel, R. et al., "Monoclonal antibodies defining the cluster-5A small cell lung carcinoma antigen," *Br. J. Cancer*, 63(S. XIV):29-32, 1991.
Zarn, J. A. et al., "Association of CD24 with the Kinase c-fgr in a Small Cell Lung Cancer Cell Line and with the Kinase Lyn in an Erythroleukemia Cell Line," *Biochemical and Biophysical Research Communications*, 225(2):384-391, Article No. 1184, Aug. 14, 1996.
T. Soussi, 2000, "p53 Antibodies in the Sera of Patients with Various Types of Cancer: A Review", Cancer Research, vol. 60 (7):1777-1788.
A.O. Güre et al., 2000, "Serological identification of embryonic neural proteins as highly immunogenic tumor antigens in small cell lung cancer", PNAS, USA, vol. 97 (8):3783-4410.
S. Zöchbauer-Müller et al., 2002, "Molecular Pathogenesis of Lung Cancer", Annual Review of Physiology, 64:681-708.
F.P. Worden et al., 2000, "Therapeutic advances in small cell lung cancer", Exp. Opin. Invest. Drugs 9 (3):565-579.
B. Birk et al., "Cobas® Core CA 19-9 II EIA: New CA 19-9 Enzyme Immunoassay with High Correlation to Radioimmunoassays", AntiCancer Research 17:2911-2914 (1997).
Y. Fujii et al., "Characterization of a murine monoclonal antibody, 5D-4, reacting with pancreatic cancers and islets of Langerhans", Biomed & Pharmacother (1992) 46, 405-411.
J. Taylor et al., "Detection of Somatostatin Receptor Subtype 2 (SSTR2) in Established Tumors and Tumor Cell Lines: Evidence for SSTR2 Heterogeneity", Peptides, vol. 15, No. 7, pp. 1229-1236 (1994).
J. Chin et al. "Reactivity of Monoclonal Anti-Human Pancreatic Carcinoma Antibodies AR2-20 and AR1-28 With Tumors of Nonpancreatic Origin", American Journal of Pathology, vol. 126, No. 1 1987, pp. 183-193.

* cited by examiner

*Primary Examiner*—Misook Yu
(74) *Attorney, Agent, or Firm*—Morgan & Finnegan, LLP

(57) ABSTRACT

The invention provides new monoclonal antibodies and binding fragments thereof which recognize and immunoreact with cell surface antigens found on small cell lung cancer (SCLC) cells. The antibodies have tumor specificity and are useful for therapy, diagnosis, monitoring, detecting and imaging of SCLC disease and of patients having SCLC disease. The antibody-recognized SCLC-specific surface antigens can serve as targets for detecting, diagnosing, inhibiting or killing SCLC cells.

2 Claims, 11 Drawing Sheets

MoAb 37.14

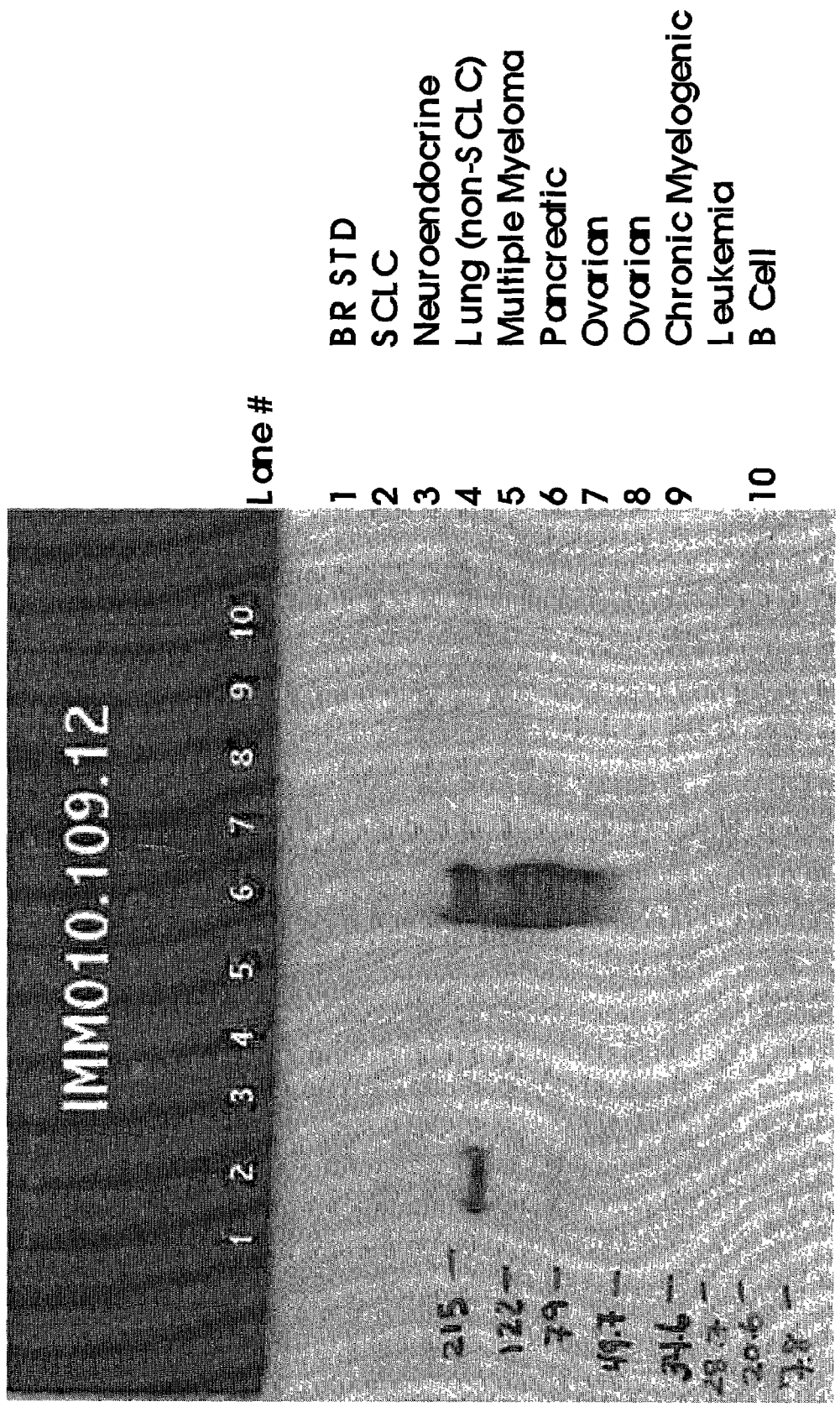

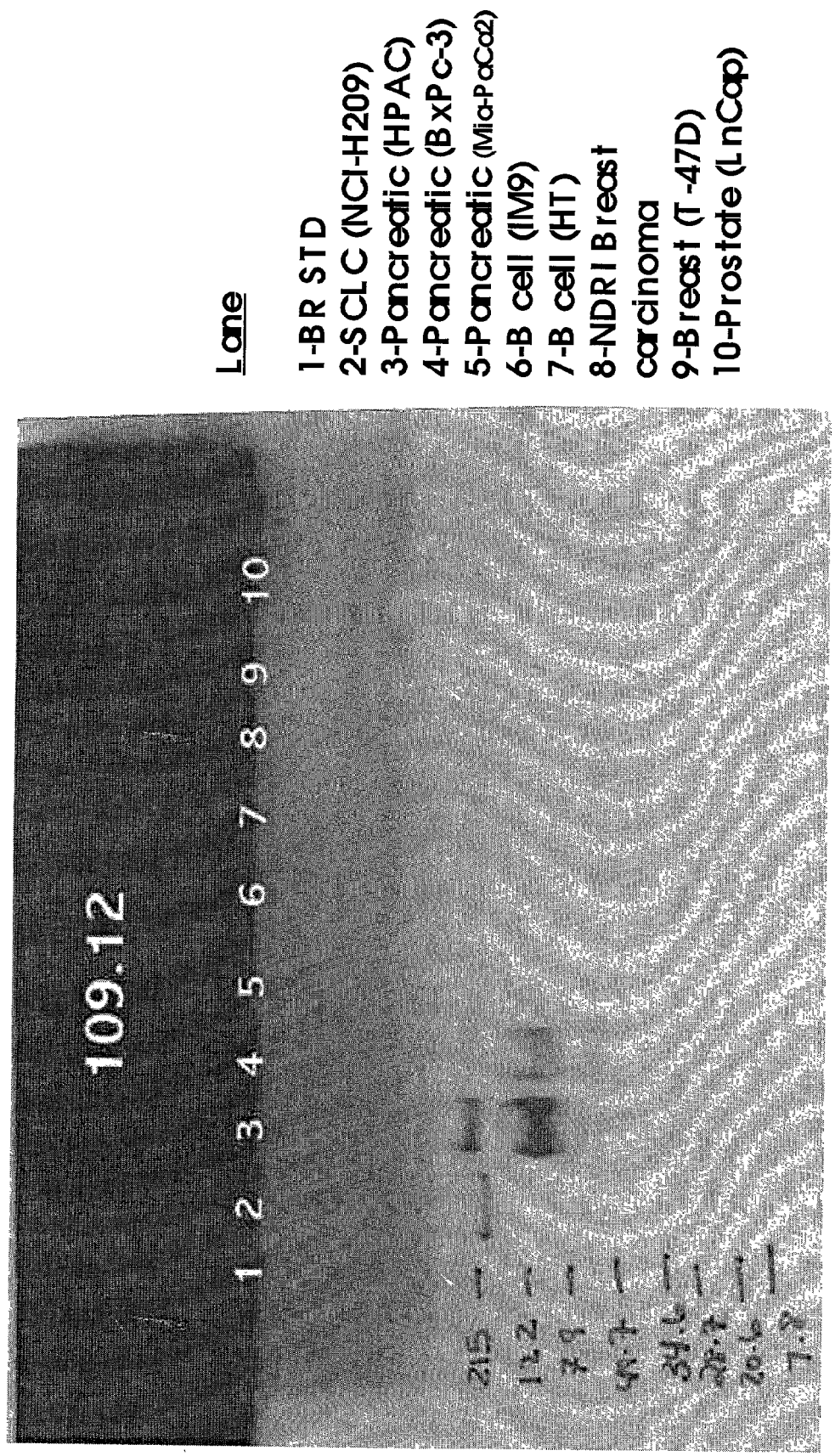

FIG. 8A
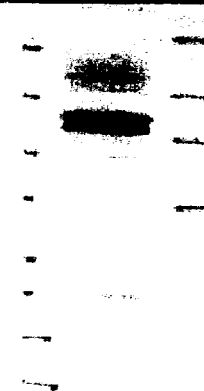
FIG. 8B

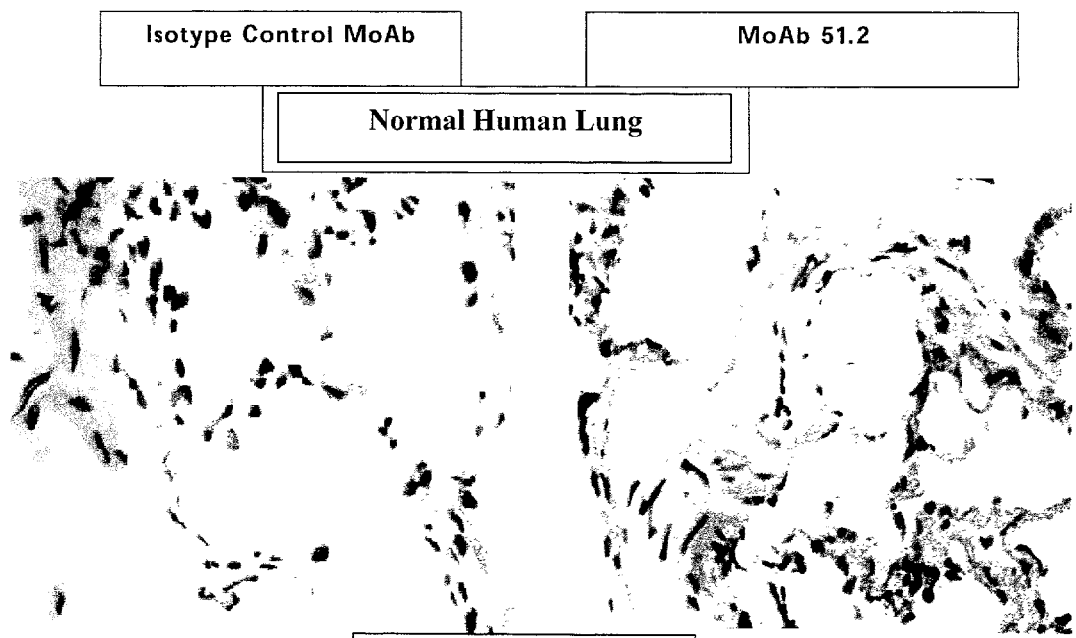
FIG. 9A　　FIG. 9B
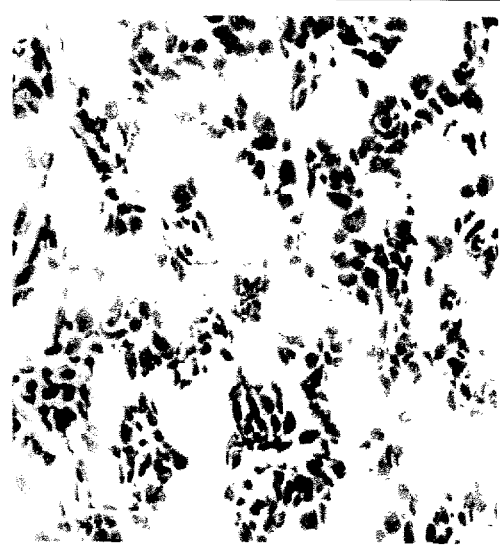
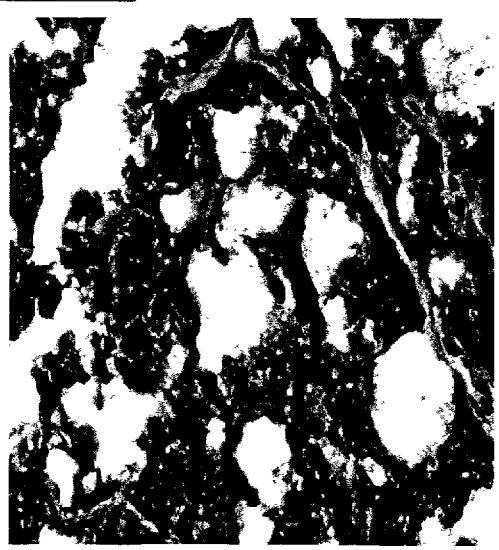
FIG. 9C　　FIG. 9D

MONOCLONAL ANTIBODIES AND CELL SURFACE ANTIGENS FOR THE DETECTION AND TREATMENT OF SMALL CELL LUNG CANCER (SCLC)

This application claims benefit of provisional application U.S. Ser. No. 60/245,340, filed Nov. 2, 2000.

FIELD OF THE INVENTION

The present invention relates generally to antibodies and more specifically to monoclonal antibodies (MoAbs), having specificity for particular cancer cells and types, as well as to methods for detecting, diagnosing, monitoring, staging, imaging and/or treating cancers, in particular, small cell lung cancer. The invention further relates to the antigens comprising epitopes on the surfaces of small cell lung cancer cells that are recognized by the MoAbs of the present invention.

BACKGROUND OF THE INVENTION

Small Cell Lung Cancer (SCLC), an aggressive form of lung cancer, represents about 20% of primary lung tumors and exhibits the most malignant phenotype of lung cancer (reviewed in Livingston, R. B., 1997, "Combined modality therapy of lung cancer", *Clin Cancer Res.*, 3:2638–47 and Gazdar, A. F., 1994, "The molecular and cellular basis of human lung cancer", *Anticancer Res.*, 13:261–68). Two thirds of patients diagnosed with SCLC are between the ages of 50 and 70, with a huge, although declining, male preponderance. There is no evidence for genetic predisposition linked with SCLC.

The predominant risk factor for SCLC is cigarette smoking. More than 95% of patients with SCLC are current or past smokers with direct correlation to both the number of cigarettes smoked per day and the duration of smoking. Ionizing radiation and occupational carcinogens are additional known risk factors for SCLC.

The natural history of SCLC differs from other types of lung cancer in the early and extensive spread of the disease. Seventy to eighty percent of the patients with SCLC have dissemination, occult or otherwise, at the time of presentation. Furthermore, SCLC has a rapid growth rate and the fastest doubling time of all of the types of lung cancer (25–160 days). The median survival time from the time of diagnosis is about 1.5 to 3 months for patients with extensive or limited disease, respectively.

SCLC usually presents as large, rapidly developing lesions arising from the centrally located tracheobronchial airways and invading the mediastinum (Stahel, R. A. et al., 1989, "Staging and prognostic factors in small cell lung cancer: A consensus report", *Lung Cancer*, 5:119–26). Typically, patients present with a cough or dyspnea, wheezing, and/or chest pain. Weight loss, fatigue and anorexia occur in up to one third of the patients. At the time of diagnosis, two thirds of the patients with SCLC have one or more clinically detectable distant metastases, including bone (30%), liver (25%), bone marrow (20%) and the central nervous system (10%). In a screening setting, sensitivity of X-ray ranges from 45–50%, sputum cytology from 25–30% and their combination amounts to about 60–70% specificity of positive diagnosis.

SCLC is a form of lung cancer characterized by a neuroendocrine phenotype. This is evidenced by the presence of neurosecretory granules visible ultrastructurally in the cytoplasm. These granules contain peptide hormones such as ADH, gastrin releasing peptide and neuromedin. The neural cell adhesion molecule is found on the cell surface. Other cell surface antigens are also linked with other forms of lung cancer. Due to their low specificity and sensitivity, tumor markers, like neuron-specific enolase (NSE), creatinin kinase BB, or neuro-endocrinological markers, are not useful in the diagnostic phase of SCLC disease. The above tumor markers are elevated in about 60–65% of cases at the time of diagnosis of SCLC and correlate with tumor bulk. The usefulness of "relapse diagnosis anticipation", i.e., the attempt to correlate the level of tumor markers with tumor progression and disease, is marginal since salvage treatments are virtually non-existent.

Since most SCLC patients are not candidates for surgery, the standard treatment for SCLC includes chemotherapy and radiotherapy in stages I–IV. SCLC is highly sensitive to initial chemotherapy. In spite of this early responsiveness, residual cells inflict a fatal relapse in most patients due to a re-emergence of chemoresistant variants. Consequently, since the cure rate is extremely low for patients with extensive SCLC disease, treatment must be considered palliative. For patients with relapsed, progressive disease, chemotherapy seldom shows clinical effectiveness or provides a lasting response.

More than 100 years ago, Paul Ehrlich proposed the use of antibodies as "magic bullets" to deliver toxins to cancer cells. The potential of targeted immunotherapy has since attracted the attention of generations of investigators. In 1975, with the development of the technology for producing monoclonal antibodies (MoAbs), (G. Kohler and C. Milstein, 1975, *Nature*, 256:495–497), it seemed that successful antibody therapy was imminent. However, early trials with monoclonal antibodies revealed significant obstacles to their use in cancer therapy. For example, immune rejection of murine monoclonal antibodies constituted the primary hurdle for making antibody therapy an effective and successful therapeutic. In addition, disappointingly low levels of cytotoxicity were reported during initial clinical experience (L. W. Kwak et al., 1995, Clinical applications of monoclonal antibodies, In: Biologic Therapy of Cancer, Eds. V. T. DeVita, Jr., S. Hellman and S. A. Rosenberg, 2nd Ed., J. B. Lippincott Co., Philadelphia, Pa., pp. 553–565).

Experience to date suggests that only a small fraction of injected antibody actually reaches a tumor (R. A. Miller et al., 1981, *Lancet*, ii:226–230). To maximize antibody binding to target molecules, an ideal antibody for cancer therapy should have a high affinity for its antigen (A. Hekman et al., 1991, *Cancer Immunol. Immunother.*, 32:364–372). In addition, an effective unconjugated antibody should work synergistically with the host's immune system effector mechanisms. Therapeutic antibodies that induce effector mechanisms such as antibody-dependent cellular cytotoxicity (ADCC) and complement-dependent cytolysis (T. A. Waldman et al., 1994, *Ann. Oncol*, 5 Suppl. 1:13–17) have the potential to provide targeted cancer therapy that is safe and effective without the use of potentially harmful conjugates such as toxins or radionuclides.

Nearly all monoclonal antibodies recognizing antigens on human cancer cells also bind to normal human cells expressing the same antigen (J. G. Jurcic et al., 1996, *Cancer Chemotherapy and Biological Response Modifiers Annual*, Eds. H. M. Pinedo, D. L. Longo and B. A. Chabner, pp. 168–188). This cross-reactivity potentially compromises therapeutic effectiveness and raises issues of toxicity, leading to the continued interest in defining antigenic targets that are unique to tumor cells.

Human SCLC is considered to be a feasible target for immunotherapy using radiolabeled monoclonal antibodies (J. Zeuthen and A. J. Vangsted, 1993, *Acta Oncologica*, 32:845–51; Y. Olabiran et al., 1994, *Br. J. Cancer*, 69:247–52; A. Smith et al., 1991, *Oncology*, 64:263–6; P. L. Beaumier et al., 1991, *Cancer Res.*, 51:676–81; R. A. Stahel, 1989, *Chest*, 96:27S-29S; and M. Hosono et al., 1994, *J. Nuclear Med.*, 35:296–300). However, SCLC-specific MoAbs isolated to date also react against one or more of neuroendocrine tissues, unrelated cells, or normal immune cells. Examples include MoAbs binding to neuronal cell adhesion molecule (NCAM), polysialic acid, cluster w4 antigen (CD24) (D. Jackson et al., 1992, *Cancer Res.*, 52:5264–70), sialoglycoprotein antigen sGP 90–135, ganglioside GD2, and ganglioside fucosyl-GM1 (FucGM1) (J. Zeuthen and A. J. Vangsted, 1993, *Acta Oncologica*, 32:845–51). A MoAb (N901), which is specific to NCAM (CD56), was reported to bind to SCLC tumors and cell lines, as well as to cardiac muscles, natural killer (NK) cells, and peripheral nerves.

Understanding the tissue distribution of tumor-associated antigens on cancers and normal tissues is essential for the selection of targets for cancer immunotherapy. The majority of cancer antigens are self-antigens that are derived from and expressed by normal cells. Frequently, the cancer antigen is identical to the normal antigen although it is expressed at higher levels or endowed with a negligible mutation insufficient for its distinction from the self-antigen. One of the escape mechanisms of malignant cells from the immune system is their resemblance to their normal cell counterparts, thereby resulting in low visibility for the malignant cells by an individual's immune surveillance system.

The process that leads to the discovery of unique cancer antigens is long, tedious and elaborate. The screening process entails an exhaustive weeding out of antigens expressed on both cancer or tumor cells and normal tissues. The probes used for the discovery of such antigens are limited in their efficacy due to the fundamentally low immunogenicity of tumor antigens. In addition, serum samples with high titers from cancer patients are generally scarce. Utilization of such probes for screening is frequently thwarted due to the "identification" of multiple artifacts, or to false-positive hits.

Antigens are diverse in their immunogenicity, i.e. their ability to stimulate the immune response. When several antigens possessing distinct immunogenic properties coexist in an antigenic preparation, their antigenic dominance regulates the intensity of the immune response to antigens. Therefore, the most robust immune response is developed against the strongest epitopes found in the antigenic preparation. Antigens with weaker immunogenicity will be disregarded, or the level of the immune response elicited against them will be negligible, due to the focus of the immune response on the stronger and more dominant epitopes. Hence, minor epitopes contained in an antigenic preparation (e.g., a vaccine) will be masked by the more immunogenic epitopes. Generating discerning MoAbs against a repertoire of minor epitopes present in an antigenic preparation (such as subcellular fractions of cancer cells) containing dominant epitopes has remained a challenge for many years.

However, in spite of the above-mentioned obstacles, the present invention provides new and specific monoclonal antibodies which are immunoreactive with SCLC cell surface antigens and which are useful in immunotherapy, diagnostic, imaging, monitoring and screening methodologies, to name a few. The present invention has solved the problem of generating myriads of non-specific antibodies by employing a technique of differential immunization, which involves, in part, tolerization with closely related antigens, e.g., on normal cells or on tumor cells exhibiting a similar phenotype, followed by immunization with the neoplastic cells of interest having unique cell surface antigen molecules. This differential/tolerization process allows the weeding out of B cells possessing undesired specificities from the entire pool of B cells, prior to the fusion of the B cells with immortalized cells to create hybridomas. Consequently, the frequency of hybridomas with the sought-after antigenic specificities is amplified in accordance with the present invention, and the entire screening process is greatly simplified.

SUMMARY OF THE INVENTION

It is an object of the present invention to provide monoclonal antibodies, or binding fragments thereof, which specifically bind to epitopes of antigen molecules present on small cell lung cancer (or cancer) cells. In accordance with the present invention, the monoclonal antibodies (specifically, e.g., MoAbs 51.2, 109.12 and 37.14) detect and bind to a single chain glycoprotein antigen having a molecular weight (MW) of about 200 kilodaltons (KDa), as determined by sodium dodecyl sulfate polyacrylamide gel electrophoresis (SDS-PAGE) under reducing conditions. In addition, MoAb 37.14 reacts with an antigen comprising two polypeptide chains, closely related in mass, and having a molecular weight of between about 35–50 KDa, thus indicating its ability to immunoreact with another epitopic site on the SCLC antigen. Yet another of the monoclonal antibodies (e.g., MoAb 26.1) binds to a SCLC-specific molecule which likely comprises a conformational epitope of a SCLC surface antigen.

Also, according to the present invention, the anti-SCLC antibodies preferably do not bind to any appreciable extent to antigens present on human neuroendocrine cell lines (e.g., neuroblastoma), or to antigens present on human multiple myeloma (MM) cells (e.g., RPMI 8226 and U266), or to antigens present on normal cells (e.g., normal lung cells). In particular, representative monoclonal antibodies of the present invention having high specificity to antigenic epitopes present on surface molecules of SCLC cells are identified herein as MoAbs IMM010.26.1 (26.1), IMM010.141.7 (141.7), IMM010.92.7 (92.7), IMM010.37.14 (37.14), IMM010.51.2 (51.2), IMM010.109.12 (109.12), IMM010.26.5 (26.5), IMM010.106.3 (106.3), IMM010.43.7 (43.7), IMM010.142.1 (142.1), IMM010.37.26 (37.26) and IMM010.21.7 (21.7).

Hybridomas producing monoclonal antibodies IMM010.26.1 (26.1), IMM010.37.14 (37.14), IMM010.51.2 (51.2), and IMM010.109.12 (109.12) have been deposited with the American Type Culture Collection (ATCC, P.O. Box 1549, Manassas, Va. 20108) on Aug. 10, 2000 under the provisions of the Budapest Treaty on the International Recognition of the Deposit of Microorganisms for the Purposes of Patent Procedures, and assigned accession numbers PTA-2359, PTA-2358, PTA-2360, PTA-2357, respectively, and incorporated by reference.

Another object of the present invention relates to antibodies that are capable of binding to the same antigenic determinant on SCLC as do the monoclonal antibodies described herein, particularly, the monoclonal antibodies produced by the hybridoma cell lines deposited with the American Type Culture Collection (ATCC), 10801 University Boulevard, Manassas, Va., 20110-2209, on Aug. 10, 2000 and having ATCC Accession Nos. PTA-2360 and PTA-2357 (51.2 and 109.12, respectively), and to binding fragments of a monoclonal antibody capable of binding the same antigenic determinants as the monoclonal antibodies described herein, particularly, the monoclonal antibodies produced by the hybridoma cell lines deposited with the American Type Culture Collection having ATCC Accession Nos. PTA-2360 and PTA-2357 (MoAbs 51.2 and 109.12, respectively).

Another object of the present invention relates to antibodies that are capable of binding to the same antigenic determinant on SCLC as do the monoclonal antibodies described herein, particularly, the monoclonal antibody produced by the hybridoma cell line deposited with the American Type Culture Collection (ATCC) on Aug. 10, 2000 and having ATCC Accession No. PTA-2358 (MoAb 37.14), and to binding fragments of a monoclonal antibody capable of binding to the same antigenic determinants as the monoclonal antibody described herein, particularly, the monoclonal antibody produced by the hybridoma cell line deposited with the American Type Culture Collection (ATCC) and having ATCC Accession No. PTA-2358 (MoAb 37.14).

It is another object of the present invention to provide a hybridoma cell line, produced by hybridoma technology as known in the art, which produces a monoclonal antibody that specifically binds to epitopes on surface antigens on SCLC cells. The antigens recognized by the antibodies of this invention comprise a single chain glycoprotein antigen having a molecular weight (MW) of about 200 kilodaltons (KDa), as determined by SDS-PAGE under reducing conditions, and an antigen, possibly a breakdown product of the 200 KDa antigen, comprising two polypeptide chains, closely related in mass, and having a molecular weight of between about 35–50 KDa, as determined by SDS-PAGE under reducing conditions. Nonlimiting examples of clonally derived hybridoma cell lines include the subcloned monoclonal antibody-producing hybridoma cell lines designated 51.2, 109.12 and 37.14. Also in accordance with the present invention are monoclonal antibodies that recognize conformational epitopes on SCLC cell surface antigen molecules, such as the 26.1 monoclonal antibody described herein.

Another object of the present invention is to provide hybridoma cell lines deposited at the American Type Culture Collection (ATCC) on Aug. 10, 2000, and designated as IMM010.109.12 (109.12), ATCC Designation No. PTA-2357; IMM010.37.14 (37.14), ATCC Designation No. PTA-2358; IMM010.26.1 (26.1), ATCC Designation No. PTA-2359; and IMM010.51.2 (51.2), ATCC Designation No. PTA-2360.

It is yet another object of the present invention to provide isolated cell surface glycoprotein antigens of SCLC comprising epitopes that are recognized and bound by the monoclonal antibodies described herein. In accordance with the present invention, these antigens are not present, or are present in significantly lower amounts, preferably at undetectable levels, on normal human cells, human multiple myeloma cells, or neuroendocrine cells of related origin. In addition, the antigens comprise (i) a single glycosylated polypeptide having a molecular weight of about 200 KDa, as well as (ii) an antigen molecule having two polypeptide chains of similar molecular mass and being in a molecular weight range of between about 35–50 KDa. The properties of these recognized antigens were determined by SDS-PAGE under reducing conditions. The isolated SCLC surface antigen according to (i) above is specifically recognized by monoclonal antibodies 51.2, 109.12 and 37.14 as described herein; the isolated SCLC surface antigen according to (ii) above is specifically recognized by monoclonal antibody 37.14 herein.

Yet another object of the present invention is to provide methods of inhibiting or killing SCLC in an individual afflicted with SCLC, by administering one or more of the monoclonal antibodies, for example, either alone, or together with others of the antibodies in a cocktail, or one or more binding fragments thereof, or administering a mixture of intact antibody(ies) and binding fragment(s) thereof, under conditions sufficient for the binding of the one or more monoclonal antibodies, or binding fragment thereof, to the SCLC cells, so as to result in the inhibition or the killing of the cancer cells by the immune cells of the individual. In accordance with one embodiment of the present invention, the monoclonal antibody, or binding fragment thereof, is conjugated to a toxic or a cytotoxic moiety, such as a chemotherapeutic agent, a photoactivated toxin, or a radioactive agent as described herein.

It is a further object of the present invention to provide a conjugate of the monoclonal antibody, or binding fragment thereof, and a toxic or cytotoxic moiety, for killing or inhibiting SCLC cells.

Another object of the present invention is to provide anti-idiotypic antibodies that mirror the binding site(s) of the monoclonal antibodies according to the present invention, and which are specific for SCLC epitopes, e.g., conformational epitopes, recognized by the antibodies of this invention. Such anti-idiotypic antibodies may be used for the treatment of SCLC by active immunization.

It is another object of the present invention to provide monoclonal antibodies having specificity to SCLC, or binding fragments thereof, bound to a solid support, substrate or matrix. Also, according to the present invention, the described monoclonal antibodies, or binding fragments thereof, can be labeled with a detectable label, such as a fluorophore, a chromophore, a radionuclide, or an enzyme, for use as diagnostic, therapeutic, imaging, and screening compounds, for example.

It is yet another object of the present invention to provide a method for localizing SCLC in a patient by administering one or more of the monoclonal antibodies described herein, or binding fragments thereof, to bind to the cancer cells or tumor cells within the patient and determining the location of the one or more monoclonal antibodies, or binding fragments thereof, within the patient. For such methods, the monoclonal antibodies, or binding fragments thereof, are preferably labeled with a detectable and physiologically acceptable label, such as a radionuclide.

A further object of the present invention provides the detection of the cell surface antigens, e.g., glycoproteins, as described herein in a body fluid sample, to aid in the diagnosis of SCLC, or other cells expressing an epitope recognized by one or more of the antibodies herein, by detecting the antigen shed, sloughed off, or released from the cancer or tumor cells into a body fluid, for example, in blood or serum. In addition, according to the present invention, the stage of the disease, and/or the effectiveness of anticancer therapies, can be monitored by determining the levels or changes over time of the specifically recognized SCLC surface antigen in the body fluid.

It is another object of the present invention to provide pharmaceutical compositions comprising one or more of the monoclonal antibodies, or binding fragments thereof, and a pharmaceutically acceptable carrier, diluent, or excipient.

Further objects and advantages afforded by the present invention will be apparent from the detailed description hereinbelow.

DESCRIPTION OF THE DRAWINGS

The appended drawings of the figures are presented to further describe the invention and to assist in its understanding through clarification of its various aspects.

As shown in FIG. 2, MoAb 51.2 detected an antigen present most significantly on SCLC cells and having a MW of about 200 KDa. The appearance of a single fuzzy band indicates that the molecule recognized by MoAb 51.2 is a single chain glycoprotein. A faint band appeared in the neuroblastoma lane 2, which contained cell membranes from a pool of neuroendocrine cells (i.e., SK-N-AS, MC-IXC and Be(2)-M17), but was absent in the myeloma (MM) lane 3, which consisted of cell membranes from a pool of MM cells (RPMI 8226 and U266). This result may indicate that the recognized antigen is over-expressed or amplified in the SCLC cells, compared with the closely-related neuroblastoma cells, which are neuroendocrine in origin. MM cells, which are more developmentally distant from SCLC cells than are neuroblastoma cells, do not appear to express the recognized antigen.

As shown in FIG. 3, MoAb 109.12 detected an antigen present significantly on SCLC cells and having a MW of about 200 KDa. The appearance of a single fuzzy band indicates that the molecule recognized by MoAb 109.12 is a single chain glycoprotein. The control membrane preparations containing cell membrane s from a pool of neuroendocrine cells (i.e., SK-N-AS, MC-IXC and Be(2)-M 17), lane 2, and cell membranes from a pool of MM cells (i.e., RPMI 8226 and U266), lane 1, were not stained by MoAb 109.12.

As shown in FIG. 4, MoAb 37.14 detected an SCLC antigen having a MW in the range of about 35–50 KDa. This antigen appeared to consist of two fragments or chains, which were closely related in mass. The control membrane preparations from a pool of neuroendocrine cells (i.e., SK-N-AS, MC-IXC and Be(2)-M 17), lane 2, and from a pool of MM cells (i.e., RPMI 8226 and U266), lane 1, were not stained by MoAb 37.14.

FIGS. 6A and 6B present the results of tumor specificity studies employing a representative anti-SCLC antibody according to the present invention. In FIG. 6A, membranes prepared from human SCLC tissue (NCI-H209), human neuroendocrine tissue (Be(2)-M17), human (non-SCLC) lung tissue (NCI-H2106), human multiple myeloma tissue (RPMI-8226), human pancreatic tissue (HPAC), human ovarian tissues (fresh ovarian tissue and MDAH-2774), human chronic myelogenous leukemia tissue (K562) and a human B cell tumor (Namalwa) were fractionated on a SDS-gel (4–20%). The gel was blotted onto nitrocellulose and incubated with the representative IMM010.109.12 MoAb. In FIG. 6B, membranes prepared from human SCLC tissue (NCI-H209), human pancreatic tissues (HPAC, BxPc-3 and Mia-PaCa2), human B cell tumors (IM9 and HT), human breast tissues (fresh breast tissue and T-47D) and human prostate tissue (LnCap) were fractionated on a SDS-gel (4–20%). The gel was blotted onto nitrocellulose and incubated with IMMOI0.109.12 MoAb of the present invention.

FIG. 7A: Intracellular staining of human neuroendocrine cancer cells (Be(2)-M17) with MoAb IMM010.51.2 (MoAb 51.2). Cells were stained extracellularly with IMM010.51.2. After fixation and permeabilization, cells were stained intracellularly with phycoerythrin (PE)-conjugated monoclonal antibody or a PE-conjugated isotype control. In the histograms, the solid, filled in area represents the amount of staining detected by the isotype control antibody. The darker, thicker line represents the amount of staining detected by the anti-mouse Ig antibody. FIG. 7B: Intracellular staining of human SCLC cells (NCI-H209) with MoAb IMM010.51.2. Cells were stained extracellularly with IMM010.51.2. After fixation and permeabilization, cells were stained intracellularly with a PE-conjugated Ig antibody or a PE-conjugated isotype control. In the histograms, the solid, filled in area represents the amount of staining detected by the isotype control antibody. The darker, thicker line represents the amount of staining detected by the anti-mouse lg antibody.

FIGS. 8A and 8B shows that monoclonal antibody 109 (MoAb 109.12) identifies a 2-subunit SCLS-antigen of lower MW following treatment of SCLC cell membranes with detergent. Cell membranes were extracted from SCLC cultures of NCI-H209 cell lines (Example 1). Part of the membrane preparation was solubilized with NP-40 (2%). The membrane preparations were fractionated on an SDS gradient gel (4–20%), which was blotted onto nitrocellulose and incubated with MoAb 109.12. FIG. 8A depicts the protein scan of fractionated SCLC cell membranes following staining of the gel with Coomasie Blue. FIG. 8B depicts a scan of Western Blots of SCLC cell membrane, unsolubilized (i.e., (−) Detergent) compared with solubilized (i.e., (+) Detergent) with NP-40 and incubated with MoAb 109.12. Detergent treatment of SCLC membranes was shown to convert the single chain, high MW approximately 200 KDa antigen into a two-subunit, lower MW antigen as shown in FIG. 8B.

FIGS. 9A–9D illustrate the results of an immunohistochemical study using a representative monoclonal antibody according to the present invention, MoAb 51.2, versus an isotype-matched control monoclonal antibody on clinical samples. The results indicate the specific and preferential immunoreactivity of 51.2 MoAb with cancerous tissue excised from SCLC patients compared with the lack of immunoreactivity with normal human lung sections. FIG. 9A shows the result of the control MoAb used to stain normal human lung tissue; FIG. 9B shows the result of MoAb 51.2 staining of normal human lung tissue. FIG. 9C shows the result of control MoAb staining of human SCLC tissue; FIG. 9D shows the result of MoAb 51.2 staining of human SCLC tissue.

DETAILED DESCRIPTION OF THE INVENTION

Figure 1:
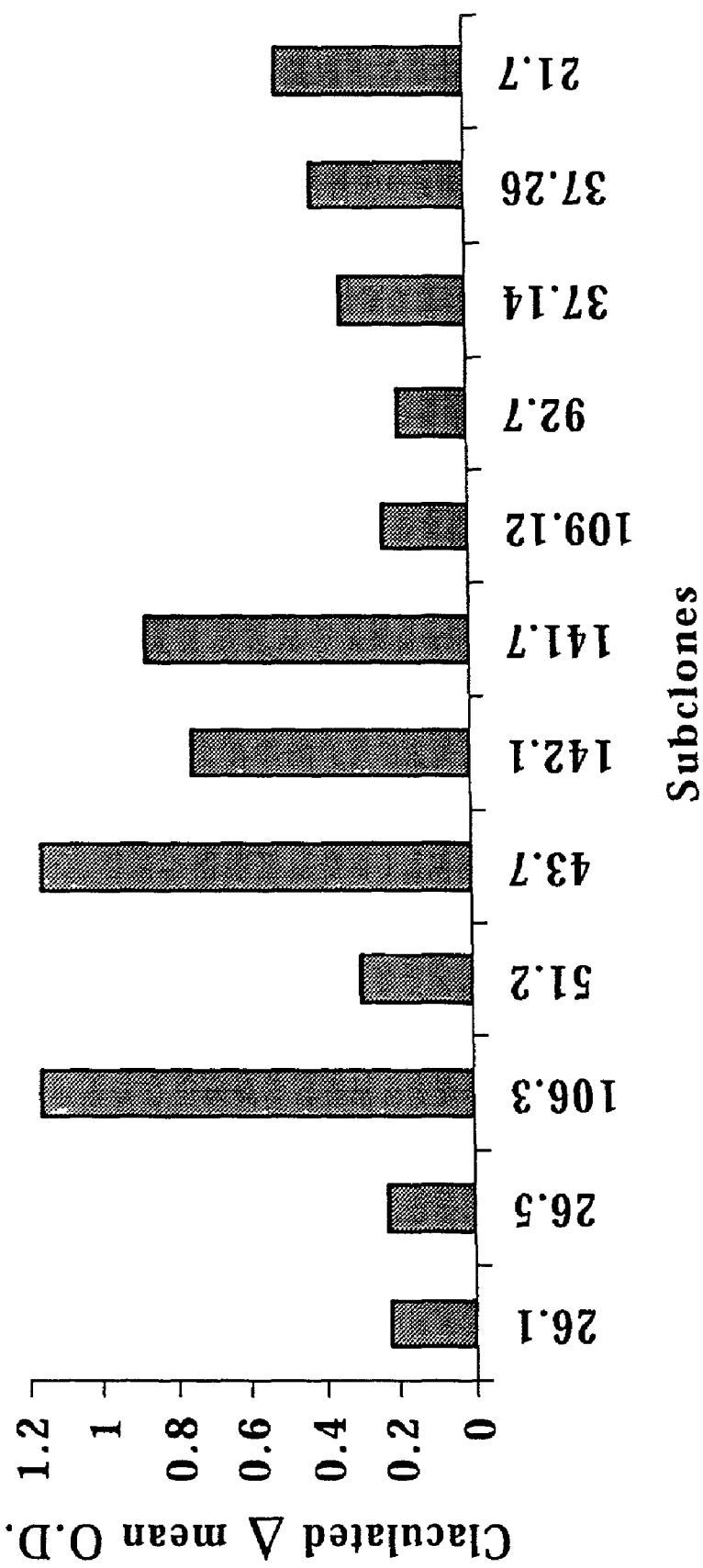
FIG. 1 presents the results of an ELISA immunoassay which demonstrates that the monoclonal antibodies as described herein exhibit high binding specificity to cell surface antigens present on SCLC cells.

The identification of unique cancer antigens enables the design of selective immunotherapy for neoplastic diseases. The capacity to utilize a determinant that is exclusively expressed by cancer cells or tumor cells, but that is not present in normal cells and tissues, insures the targeting and elimination of the neoplastic cells, while insulating the viability and function of the normal cells. For many malignancies and carcinomas, novel cancer antigens have not been defined, and antibodies immunoreactive with specific cancer antigens have not been found.

The majority of cancer antigens are self-antigens, or auto-antigens, that are derived from and expressed by normal cells. Frequently, the cancer antigen is identical to the normal counterpart cell antigen, although it is expressed at higher levels, or is endowed with a negligible mutation that is not sufficient to allow it to be distinguished from the self-antigen. One of the escape mechanisms of malignant cells from the surveillance of the immune system is the general phenotypic similarity of the malignant or cancer cells to their normal cell counterparts, thus resulting in the low visibility of the malignant or cancer cells in the immune system and their general escape from eradication by the immune surveillance cells.

The present invention provides monoclonal antibodies that specifically recognize and bind to epitopes on cell surface antigens expressed by tumor cells or cancer cells of small cell lung carcinoma or cancer (SCLC). A number of the monoclonal antibodies described herein have been found to recognize and bind to surface glycoprotein molecules that are either exclusively present, or highly expressed, on SCLC cells, but which are absent from, or less highly expressed or displayed, on developmentally related neuroendocrine cells which serve as controls. In addition, the SCLC-specific antigens recognized by the monoclonal antibodies described herein are absent from or undetectable on unrelated cancer cells, such as multiple myeloma cells. The newly-discovered SCLC-specific surface antigens provide targets for therapeutic intervention in SCLC disease, as well as for diagnostic and cell purification purposes.

In one aspect of the present invention, the use of a differential immunization protocol allows the focusing of the humoral immune response in an immunized animal host (including humans) to cancer antigens uniquely expressed on SCLC cells. The immune response by the host is robust and results in the elicitation of enhanced concentrations of serum antibodies having superior affinity to immunogen. In this way, monoclonal antibodies having specificity and high affinity for SCLC surface antigens can be produced and used in compositions for treatments and therapies for patients having SCLC disease, as well as in diagnostic and/or screening protocols for determining and/or monitoring disease.

In another aspect of the present invention, a technique known as contrasting immunization is used to obtain monoclonal antibodies to antigen, in particular, SCLC-specific antigen, and to identify the SCLC antigens described herein. Two divergent immunogens provided at different anatomical locations are used (e.g., Example 1). The dual immunization polarizes the migration of the distinct populations of immune cells to discrete draining lymph nodes. For example, a pool of human SCLC cell lines is used as the immunogen to obtain murine monoclonal antibodies to an antigen specific to SCLC. A high dose of control cells, which constitute a pool of related neuroendocrine cell lines, is used to polarize the immune response, so as to effectively delete undesired immune cells from the lymph nodes near to the site of immunization with the desired antigen. The immune cells extracted from the draining lymph nodes close to the site of immunization with the desired SCLC cell immunogens are then immortalized by fusion with murine myeloma cells, using hybridoma protocols known and practiced in the art. Following this type of immunization protocol, for example, the antipodal draining lymph nodes are populated with immune cells specific to the control, or undesired, cell immunogens, thereby allowing the SCLC-specific immune cells to be "captured" in the node close to the site of immunization with the SCLC cells as immunogen. Other methods of immunization and protocols for eliciting an immune response can be considered to be suitable for generating antibodies according to the invention, see, for example, WO 99/44583.

The induction of high zone tolerance to an antigen or set of antigens can be viewed as reshaping the repertoire of the immune system. Immunizing the animal with a lower dose of antigen evokes a strong humoral response against the minor or weak epitopes due to their liberation from the shadow created by the dominant epitopes.

Tolerance is the failure of the immune system to respond to an antigen. Tolerance to self-antigen is an essential feature of the immune system that prevents self-inflicted damage to the host's tissues and organs. When tolerance is lost, the immune system can destroy self-tissues, as happens in autoimmune diseases. Autoimmune disorders are rare and are known to be linked to HLA gene composition. The precipitating event that leads to the collapse of self-tolerance is unknown, but is suspected to be associated with infectious agents. The deliberate rupture of tolerance is a major challenge and can be achieved for some antigens using repetitive immunizations in the presence of extremely powerful adjuvants.

The production of a monoclonal antibody to a non-dominant, (e.g., self-antigen), epitope is often desired, but may be hindered, because known immunodominant epitopes overwhelm the immune response. A technique such as contrasting or differential immunization with antigen allows focused antibody responses targeting the desired epitope by changing the hierarchy of the antigen dominance. By tolerizing the immunized host against the dominant epitopes, the minor or weaker antigens are "liberated" from the overbearing shadow of the dominant epitopes and, hence, are briskly reacted against by the cells of the immune system. One way to produce monoclonal antibodies directed to an array of non-dominant epitopes is by essentially tolerizing immunized animals to the immunodominant epitopes, followed by immunization with the non-dominant epitopes, e.g., those epitopes present on the surface antigens of SCLC cells.

The differential or contrasting immunization strategy is also able to detect antigens that are of broad chemical diversity. This unique capability can be applied to the discovery of antigens of importance in areas where gene discovery and gene product technology are unable to function due to the limitation of these technologies for use in the discovery of protein markers and products. Because this type of immunization is suitable for generating monoclonal antibodies against a broad range of chemically diverse antigens, the technology is applicable for the development of protein markers and therapeutic products pertaining to cancers, tumors (both benign and malignant), infectious agents, stem cell transplantation, neurodegenerative diseases, cardiovascular diseases, autoimmune diseases, allergic diseases and inflammatory diseases.

For example, the contrasting immunization protocol is used to tolerize mice to a pool of human neuroendocrine cells, e.g., the neuroblastoma cell lines SK-N-AS, Be (2)-M17, and MC-IXC (Example 1), which are closely related by lineage to SCLC cells. The tolerized mice are then immunized with a pool of three human SCLC cell lines. Serum from mice immunized with the differential protocol contain antibodies that are specific to human SCLC cells, while serum from mice immunized using conventional methods are devoid of such SCLC cancer-specific antibodies.

Figure 2:
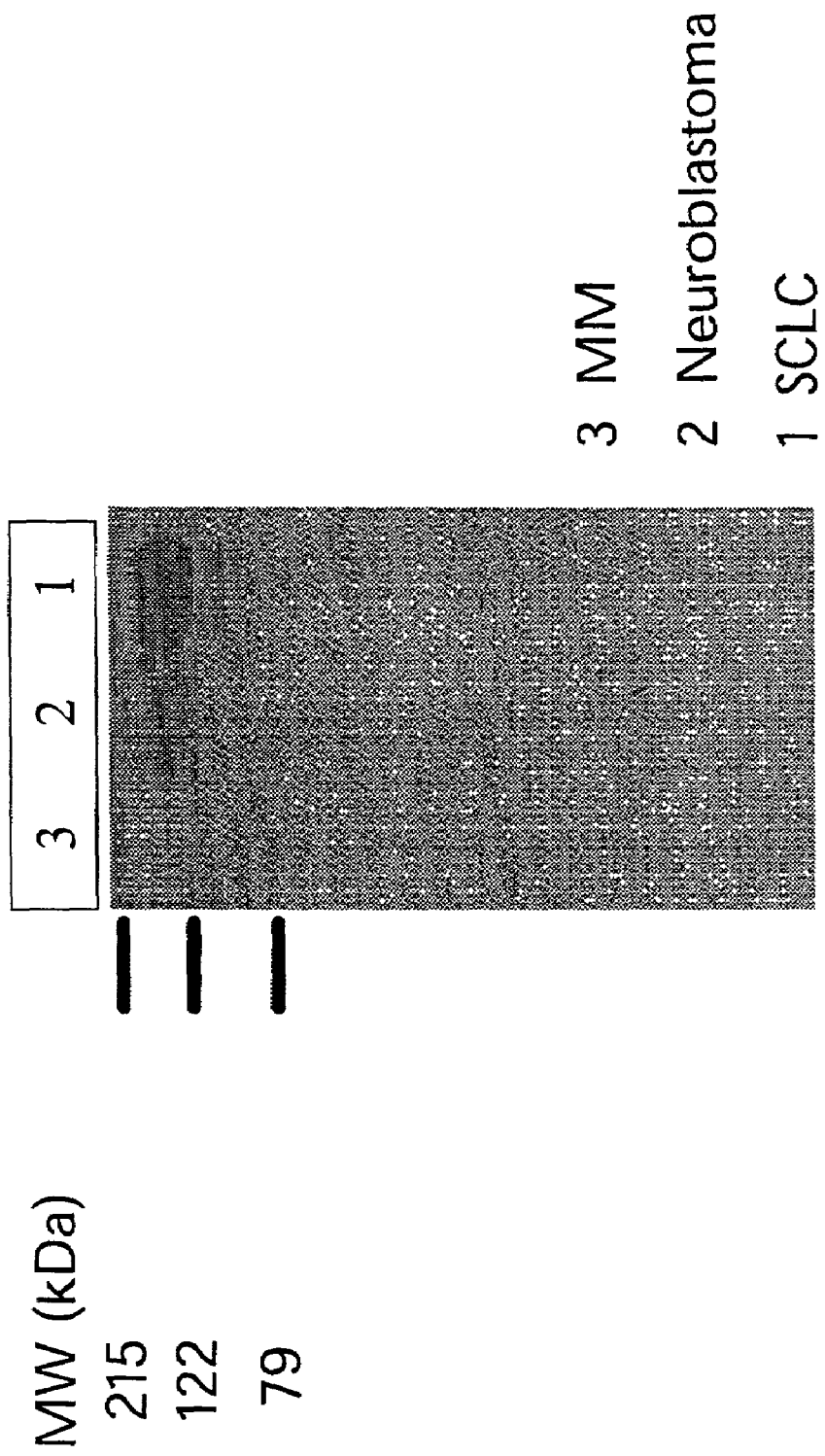
FIG. 2 shows the results of a scan of a Western Blot performed under reducing conditions to assess the specificity of the monoclonal antibody 51.2 (MoAb 51.2) for SCLC antigen. All lanes contained an equal total concentration of membrane preparation from the designated cell lines. The membrane preparation is loaded on an SDS gel in an amount of 50 micrograms per lane. Lane 1: SCLC cell membranes; lane 2: neuroblastoma cell membranes; lane 3: multiple myeloma (MM) cell membranes.
Figure 3:
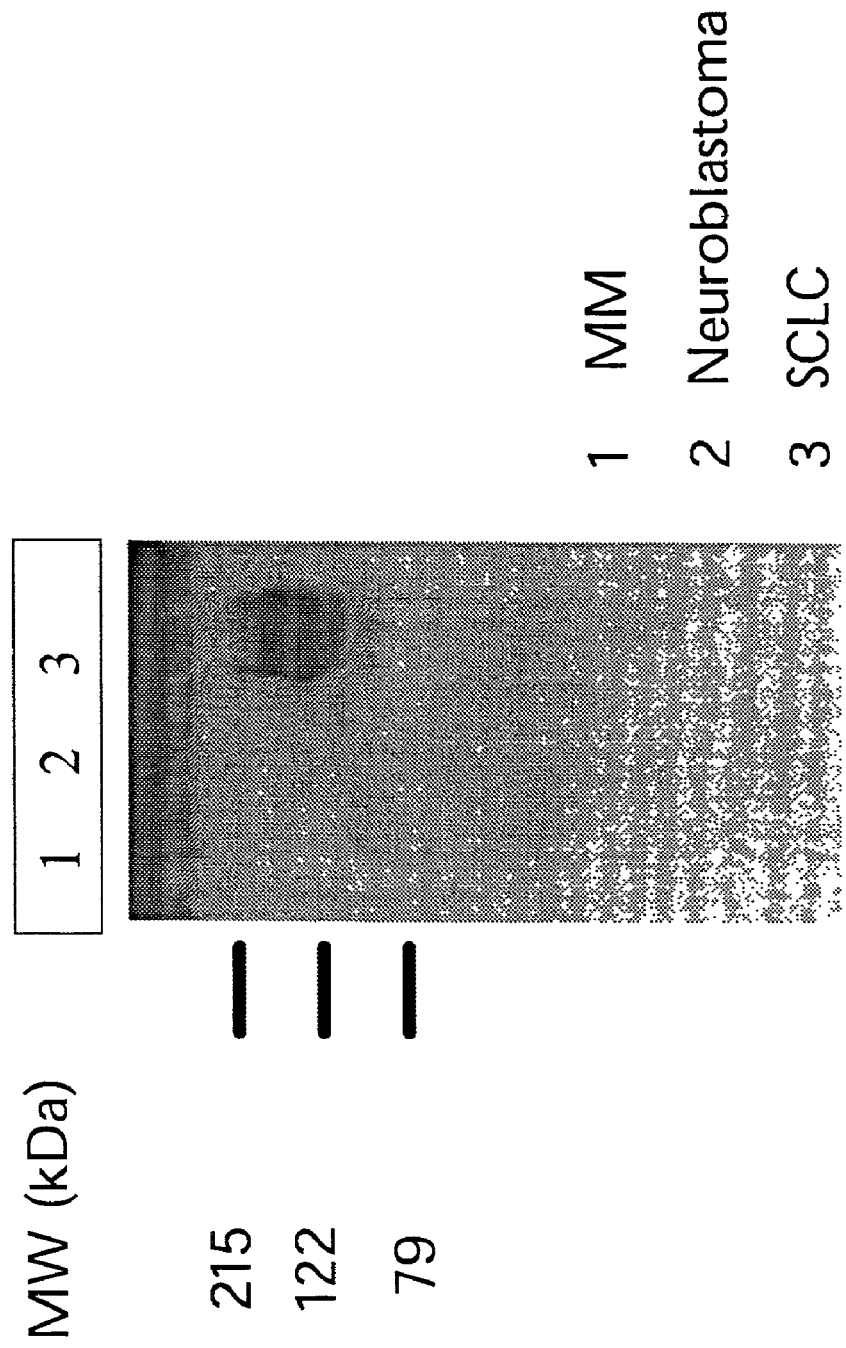
FIG. 3 shows the results of a scan of a Western Blot performed under reducing conditions to assess the specificity of the monoclonal antibody 109.12 (MoAb 109.12) for SCLC antigen. All lanes contained an equal total concentration of membrane preparation from the designated cell lines. Lane 1: multiple myeloma (MM) cell membranes; lane 2: neuroblastoma cell membranes; lane 3: SCLC cell membranes.

The present invention provides the discovery of new monoclonal antibodies (MoAbs) directed against cancer-specific antigen(s) expressed on human SCLC cells. Preferred is the use of the contrasting or differential immunization technique to elicit monoclonal antibodies having specificities toward surface antigen or marker epitopes of SCLC cancer or tumor cells. The monoclonal antibodies were characterized and found to bind specifically to antigens on the surface of SCLC cells. In particular, three representative, exemplary monoclonal antibodies were isolated, characterized and found to react specifically with a single chain SCLC cell surface glycoprotein with a MW of about 200 KDa (as determined by SDS-PAGE under reducing conditions) present on SCLC cells (FIGS. 2, 3 and 8B). These MoAbs were given the designations 51.2, 37.14 and 109.12 (ATCC Designation Nos. PTA-2360, PTA-2358 and PTA-2357, respectively). MoAb 109.12 was found not to react with developmentally related neuroendocrine cells, i.e., neuroblastoma cell lines, or unrelated human multiple myeloma (MM) cancer cells. MoAb 51.2 reacted only minimally with neuroendocrine cells and not at all with MM cells.

The representative isolated monoclonal antibody, 37.14, was also found to react specifically with a cell surface glycoprotein having MW of between about 35–50 kDa as determined by SDS-PAGE under reducing conditions. This antibody was deposited with the ATCC under ATCC Designation No. PTA-2358. The 35–50 kDa antigen appeared to be comprised of two chains or fragments, closely related in mass. The 37.14 antibody did not recognize any similar antigen on either neuroendocrine cells or unrelated MM cells.

Yet another representative isolated monoclonal antibody, MoAb 26.1 (deposited with the ATCC under ATCC Designation No. PTA-2359), was found to recognize a SCLC-specific cell surface molecule as assayed under conditions for FACS analysis. However, this antibody did not appear to react with SCLC-membranes in Western Blot assays performed under reducing conditions. Such a result suggests that the epitope recognized by MoAb 26.1 is a conformational epitope that is destroyed by linearization under the conditions for Western Blotting involving the use of SDS.

Another embodiment of the present invention relates to monoclonal antibodies, and binding fragments or portions thereof, which recognize the foregoing SCLC cell surface glycoproteins. Thus, the present invention encompasses the deposited monoclonal antibodies, as well as antibodies, preferably monoclonal antibodies, and their binding fragments, having specificity for the above-described antigens present on SCLC cells. Nonlimiting examples of antibody fragments or antigen bindable fragments that bind to epitopes on the SCLC antigens include the following: Fab fragments, F(ab)$_2$ fragments, Fab' fragments, fragments produced by F(ab) expression libraries, F(ab')$_2$ fragments, Fd fragments, Fd' fragments and Fv fragments. The antibodies may be human, or from animals other than humans, preferably mammals, such as rat, mouse, guinea pig, rabbit, goat, sheep, and pig. Preferred are mouse monoclonal antibodies and antigen-binding fragments or portions thereof. In addition, chimeric antibodies and hybrid antibodies are embraced by the present invention.

In accordance with the present invention, the monoclonal antibodies and binding fragments thereof may be characterized as those which are 1) produced from the hybridoma cell lines deposited at the American Type Culture Collection, 10801 University Boulevard, Manassas, Va., 20110-2209 under ATCC Accession Nos. PTA-2357, PTA-2358, PTA-2359 and PTA-2360; 2) antibodies that are capable of binding to the same antigenic determinant as does the monoclonal antibody produced by the hybridoma cell lines deposited at the American Type Culture Collection under ATCC Accession Nos. PTA-2357, PTA-2358, PTA-2359 and PTA-2360; 3) binding fragments of the monoclonal antibodies produced by the hybridoma cell lines deposited at the American Type Culture Collection under ATCC Accession Nos. PTA-2357, PTA-2358, PTA-2359 and PTA-2360; or 4) binding fragments of a monoclonal antibody capable of binding to the same antigenic determinant as does the monoclonal antibody produced by the hybridoma cell lines deposited at the American Type Culture Collection under ATCC Accession Nos. PTA-2357, PTA-2358, PTA-2359 and PTA-2360. The immunoglobulin isotypes of the deposited monoclonal antibodies of the present invention are presented in Table 1 as follows:

TABLE 1

| MoAb | Isotype (H, L chain) |
| --- | --- |
| 21.7 | IgG1, kappa |
| 26.1 | IgG1, kappa |
| 37.14 | IgG2a, kappa |
| 51.2 | IgG2a, kappa |
| 109.12 | IgG1, kappa |

According to the present invention, the monoclonal antibodies recognize specific glycoprotein surface antigens expressed by and present on SCLC cells. The glycoprotein surface antigen recognized by a subset of the monoclonal antibodies as represented by MoAb 37.14, MoAb 51.2 and MoAb 109.12, ATCC Accession Nos. PTA-2358, PTA-2360 and PTA-2357, respectively, is a single polypeptide having a molecular weight of about 200 KDa as determined by SDS-PAGE under reducing conditions. The glycoprotein surface antigen, or epitope, recognized by another subset of the monoclonal antibodies represented by MoAb 37.14, ATCC Accession No. PTA-2358, has a molecular weight of about 35–50 KDa as determined by SDS-PAGE under reducing conditions. SCLC-specific antigens recognized by others of the monoclonal antibodies according to the present invention contain conformational epitopes, whose recognition by the monoclonal antibodies as represented by MoAb 26.1 is dependent on the conformational nature of the antigen being intact and not denatured, degraded, linearized, or otherwise adversely affected.

The present invention further provides hybridoma cell lines that produce a monoclonal antibodies that specifically bind to antigens on the surface of SCLC cells as described and characterized herein. Methods for preparing hybridoma cell lines are well known and practiced in the art. Accordingly, any technique or protocol that results in the production of homogeneous populations of antibody molecules to a specific antigen, preferably monospecific antibody molecules, e.g., monoclonal antibodies, by continuous cell lines in culture may be used. Such techniques include, but are not limited to, the hybridoma technique developed by Kohler and Milstein (1975, *Nature*, 256:495–497), the trioma technique, the human B-cell hybridoma technique (Kozbor et al., 1983, *Immunology Today*, 4:72; Cote et al., 1983, *Proc. Nat'l Acad. Sci. USA*, 80:2026–2030), as well as the Epstein Barr Virus (EBV)-hybridoma technique to produce human monoclonal antibodies (Cole et al., 1985, *In: Monoclonal Antibodies and Cancer Therapy*, Alan R. Liss, Inc., pp. 77–96). Such antibodies may be of any immunoglobulin class, including IgM, IgG, IgE, IgA and IgD, or any subclass thereof. Hybridoma cells may be cultured in vivo or in vitro according to established methods.

In a further aspect, monoclonal antibodies can be produced in germ-free animals utilizing the technology described in International Patent Application No. WO 98/02545. Also suitable for use in the present invention are hybrid antibodies, chimeric antibodies and humanized antibodies (e.g., U.S. Pat. No. 5,585,089 to Queen et al.). Antibodies, such as hybrid or chimeric antibodies having human components, or humanized antibodies, are preferable for use in therapies of human diseases or disorders, because the human or humanized antibodies are much less likely than xenogenic antibodies to induce an immune response, particularly an allergic response, when introduced into a human host.

In addition, techniques developed for the production of chimeric antibodies (Morrison et al., 1984, *Proc. Natl. Acad. Sci. USA*, 81:6851–6855; Neuberger et al., 1984, *Nature*, 312:604–608, Takeda et al., 1985, *Nature*, 314:452–454) by splicing the genes from a mouse antibody molecule of appropriate antigen specificity together with genes from a human antibody molecule of appropriate biological activity are suitable for use in the present invention.

Further, according to the present invention, the techniques described for the production of single chain antibodies (e.g., U.S. Pat. Nos. 5,476,786 and 5,132,405 to Huston; Huston et al., 1988, *Proc. Natl. Acad. Sci. USA*, 85:5879–5883; U.S. Pat. No. 4,946,778 to R. C. Ladner et al.; Bird, 1988, *Science*, 242:423–426 and Ward et al., 1989, *Nature*, 334: 544–546) can be adapted to produce SCLC-surface antigen specific single chain antibodies. Single chain antibodies are formed by linking the heavy and light immunoglobulin chain fragments of the Fv region via an amino acid bridge, resulting in a single chain polypeptide. Univalent antibodies are also embraced by the present invention. In addition, techniques for the construction of Fab expression libraries (Huse et al., 1989, *Science*, 246:1275–1281) are suitable for use in this invention to allow the rapid and easy identification of monoclonal antibody Fab fragments, or derivatives or analogs, having the desired specificity.

Antibody fragments containing the idiotype of the specific anti-SCLC surface antigen antibodies, and which "mimic" the SCLC specific antigens, can be produced by known techniques (Greenspan and Bona, 1993, *FASEB J.*, 7(5): 437–444 and Nissinoff, 1991, *J. Immunol.*, 147(8):2429–2438). For example, such fragments include, without limitation, the $F(ab')_2$ fragment, which can be produced by pepsin digestion of the intact antibody molecule; the Fab' fragment, which can be produced by reducing the disulfide bridges of the $F(ab')_2$ fragments, and the Fab fragments, which can be generated by treating the intact antibody molecule with the enzyme papain and a reducing agent.

It is to be understood that the contrasting immunization and differential antigen immunization procedures described herein are nonlimiting examples of ways in which the desired antibodies can be obtained for their numerous uses. Accordingly, it is also envisioned that anti-SCLC antibodies can be elicited in an animal host by immunization with SCLC cells or cell-derived immunogenic components, or can be formed by in vitro immunization (sensitization) of immune cells. The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains. Using the aforementioned types of antibodies, for example, cells displaying the specifically recognized surface glycoprotein antigens, or the antigens themselves, or an immunogenic fragment or portion thereof, can be detected in a test sample by chromatography on antibody-conjugated solid-phase matrices or supports (see E. Harlow and D. Lane, 1999, *Using Antibodies: A Laboratory Manual*, Cold Spring Harbor Laboratory, Cold Spring Harbor, N.Y.), or by immunoassay. Preferred are antibodies that specifically recognize and bind to surface antigens expressed by SCLC cells; more preferred are the SCLC specific surface glycoprotein antigens described herein.

The antibodies can be employed to prepare anti-SCLC antigen antibody affinity columns. For example, gel supports or beads can be activated with various chemical compounds, e.g., cyanogen bromide, N-hydroxysuccinimide esters, and antibodies can be bound thereto. More particularly and by way of example, anti-SCLC antibodies can be added to Affigel-10 (Biorad), a gel support which is activated with N-hydroxysuccinimide esters, such that the antibodies form covalent linkages with the agarose gel bead support. The antibodies are then coupled to the gel via amide bonds with a spacer arm. The remaining activated esters are then quenched with ethanolamine HCl, 1M, pH 8. The column is washed with water, followed by 0.23M glycine HCl, pH 2.6, to remove any non-conjugated antibody or extraneous protein. The column is then equilibrated in phosphate buffered saline (PBS), (pH 7.3) with appropriate detergent, and the sample materials, i.e., cell culture supernatants or cell extracts, for example, containing SCLC surface antigen (e.g., prepared using appropriate membrane solubilizing surfactants) are slowly passed over the column. The column is washed with PBS/surfactant until the optical density falls to background. The protein is then eluted from the column with 0.23M glycine-HCl, pH 2.6/surfactant. The purified SCLC-derived glycoprotein is then dialyzed against PBS/surfactant.

In another embodiment, the present invention embraces one or more isolated surface antigens of SCLC, as described herein and as recognized and bound by the monoclonal antibodies according to this invention. In particular, the invention embraces the approximately 200 KDa single chain glycoprotein antigen of SCLC cells recognized by the 37.14, 109.12 and 51.2 monoclonal antibodies having ATCC Accession No. PTA-2358, ATCC Accession No. PTA-2357 and ATCC Accession No. PTA-2360, respectively, as well as the approximately 35–50 KDa single chain glycoprotein antigen or epitopic determinant on SCLC cells as recognized by the 37.14 monoclonal antibody having ATCC Accession No. PTA-2358. Further embraced by the present invention are cell surface glycoproteins comprising an epitope recognized by the antibodies of this invention, e.g., the 26.1 MoAb having ATCC Accession No. PTA-2359. The cell surface glycoproteins comprising the recognized conformational epitope are not present on normal cells, or on cells that are developmentally unrelated to SCLC.

Another aspect of the present invention relates to therapeutic methods for the treatment of individuals afflicted with SCLC and neuroendocrine diseases involving cells displaying the SCLC-specific surface glycoprotein(s), particularly, those having a molecular weight of about 200 KDa or of about 35–50 KDa, as determined by SDS-PAGE under reducing conditions and recognized by the antibodies according to this invention. Other dysproliferative diseases in which the glycoprotein antigens described herein are present on the cell surface are also treatable using the antibodies and methods according to this invention.

The therapeutic methods encompassed by the present invention involve primary tumors or cancers, as well as metastases. As an example, a method for inhibiting or killing SCLC cells comprises administering to a patient one or more of the monoclonal antibodies having specificity for SCLC cells, or a binding fragment thereof, as described above, under conditions sufficient for the binding of the monoclonal antibody, or binding fragment, to tumor or cancer cells in the patient. The binding of antibodies, or their binding fragments, to the tumor cells or cancer cells induces the inhibiting or killing of the cells by the patient's immune cells. The above described method employs the antibodies or their binding fragments without modification, relying on the binding of the antibodies to the surface of the SCLC cells in situ to stimulate and induce an immune response and attack by autologous immune cells thereon. However, such antibody-mediated treatment or therapy may also be accompanied by other treatments that are directed to tumor or cancer cells, for example, radiation, chemotherapy, and the like, as well as by adjunctive therapies to enhance the immune system's attack on the opsonized cancer or tumor cells following the above-described treatment/therapy procedure(s).

More specifically, a growth factor, lymphokine, or cytokine may be co-administered with one or more of the anti-SCLC monoclonal antibodies, for example, erythropoietin and/or GM-CSF, to stimulate white blood cells and support the immunocompetence status of the patient. In addition, chimeric or fusion antibodies, or other recombinant antibodies of the present invention may be used in therapies and treatment. For example, a fusion protein molecule comprising at least the antigen-binding region of an antibody of the invention joined to at least a functionally active or bioactive portion of a second protein having anti-tumor or cancer effects, e.g., a lymphokine or oncostatin, may be used to treat SCLC or tumors, particularly, in vivo. Moreover, a chimeric antibody can be prepared, wherein the antigen binding portion or site is joined to a human Fc molecule of an immunoglobulin, e.g., IgG1, to promote antibody-dependent mediated cytotoxicity or complement-mediated cytotoxicity. Recombinant techniques and protocols as known and practiced in the art (e.g., U.S. Pat. No. 4,474,893 to C. L. Reading, issued Oct. 2, 1984) may be used to construct bispecific or bifunctional chimeric antibodies wherein one of the binding specificities is that of the antibody according to the present invention.

In another of its aspects, the present invention comprises therapeutic methods utilizing the described monoclonal antibodies, or binding fragments thereof, to which a cytotoxic agent has been bound, affixed or coupled. The binding of the cytotoxic antibodies, or binding fragments thereof, to the SCLC tumor or cancer cells inhibits the growth of the cells and optimally kills the cells. Nonlimiting examples of suitable cytotoxic agents include chemotherapeutic compounds, a drug (e.g., Garnett and Baldwin, 1986, *Cancer Res.*, 46:2407–24112), a prodrug, enzymes, a photoactivated toxin, or a radioactive agent. Cytotoxic agents include, but are not limited to, ricin A chain, abrin A chain, modeccin A chain, gelonin, melphalan, bleomycin, adriamycin, daunomycin, or pokeweed antiviral proteins (PAP, PAPII, or PAP-S).

The skilled practitioner will realize that there are numerous radionuclides and chemocytotoxic agents that can be coupled to tumor-specific antibodies by well-known techniques and delivered to a site to specifically destroy tumor cells and tissue. (See, for example, U.S. Pat. No. 4,542,225 to W. A. Blattler et al., issued Sep. 17, 1985; and Pastan et al., 1986, *Cell*, 47:641–648). Nonlimiting examples of photoactivated toxins include dihydropyridine- and omega-conotoxin (Schmidt et al., 1991, *J. Biol. Chem.*, 266(27): 18025–18033). Nonlimiting examples of imaging and cytotoxic reagents that are suitable for use include $^{125}$I, $^{123}$I, $^{111}$In (e.g., Sumerdon et al., 1990, *Nucl. Med. Biol.*, 17:247–254), $^{99m}$Tc, $^{32}$P, $^{3}$H and $^{14}$C; fluorescent labels such as fluorescein and rhodamine; chemiluminescent labels such as luciferin, and paramagnetic ions for use in magnetic resonance imaging (Lauffer et al., 1991, *Magnetic Resonance in Medicine*, 22:339–342). Antibodies can be labeled with such reagents using protocols and techniques known and practiced in the art. See, for example, Wenzel and Meares, *Radioimmunoimaging and Radioimmunotherapy*, Elsevier, New York, 1983; Colcer et al., 1986, *Meth. Enzymol.*, 121:802–816; and *Monoclonal Antibodies for Cancer Detection and Therapy*, Eds. Baldwin et al., Academic Press, 1985, pp. 303–316, for techniques relating to the radiolabeling of antibodies. Yttrium-90 labeled monoclonal antibodies have been described for maximizing the dose delivered to the tumor or cancer cells and/or tissue, while limiting toxicity to normal tissues (e.g., Goodwin and Meares, 1997, *Cancer Supplement*, 80:2675–2680). Other cytotoxic radionuclides including, but not limited to, Copper-67 ($^{67}$Cu), Iodine-131 ($^{131}$I) and Rhenium-186 can also be used for labeling monoclonal antibodies directed against SCLC surface antigens.

The detectable/detecting label used is selected according to the imaging modality to be used. For example, radioactive labels, such as Indium-111 ($^{111}$In), Technetium-99m ($^{99m}$Tc), or Iodine 131 ($^{131}$I), can be used for planar scans or for single photon emission computed tomography (SPECT). Also, positron-emitting labels such as Fluorine-19 can be used in positron emission tomography (PET). Paramagnetic ions, such as Gadlinium(III) or Manganese(II) can be used in magnetic resonance imaging (MRI). The monoclonal antibodies can also be labeled with radio-opaque labels for the visualization of SCLC cells after injection, for example, by X-ray, CATscan, or MRI. In particular, for SCLC disease, localization of the label within the lung, or external to the lung, permits the determination of the spread of the disease. The amount of label that is present and detectable within the lung, for example, allows the determination of the presence or absence of cancer or tumor in the lung.

Other covalent and non-covalent modifications of the monoclonal antibodies, or their binding fragments, as described herein are further encompassed for use in the present invention. Such modifications are meant to include agents which are co-administered with, or are administered subsequent to, the administration of the antibody(ies), or fragments thereof, to induce or stimulate growth inhibition or killing of the cells to which the antibody(ies) or fragments bind. For example, immunotoxins conjugated to monoclonal antibodies have been found to be efficacious in animal models. The conjugation of MoAbs with ribosome-inactivating proteins (e.g., ricin A-chain, ricinus agglutinin, or viscumin) or photoinactivating agents has been described (see, e.g., D. B. Papkovskii et al., 1990, $Biomed.$ $Sci.,$ 1(4):401–406). In addition, pokeweed antiviral protein (PAP) has the ability to disrupt anti-apoptotic complexes or inhibit protein synthesis within the target cell, ultimately resulting in the death of the cell. Further, a number of small molecules that inhibit tyrosine kinases can be specifically targeted to cancer cells as growth factor conjugates and which can be administered with the monoclonal antibodies, or fragments thereof, according to the present invention.

In a related embodiment of the present invention, the monoclonal antibodies according to this invention can be used for immunotherapy, either unlabeled or labeled with a therapeutic agent. These therapeutic agents can be coupled either directly or indirectly to the described monoclonal antibodies, using techniques routinely practiced in the art. One example of indirect coupling is by the use of a spacer moiety. Spacer moieties, in turn, can be either insoluble or soluble (Dieher et al., 1986, $Science,$ 231:148) and can be selected to enable drug release from the monoclonal antibody molecule at the target site. Examples of therapeutic agents which can be coupled to the monoclonal antibodies of the invention for anti-cancer immunotherapy are drugs, radioisotopes, lectins, and toxins.

The drugs with which can be conjugated to the monoclonal antibodies of the present invention include non-proteinaceous as well as proteinaceous compounds. The term "non-proteinaceous drugs" encompasses compounds which are classically referred to as drugs, for example, mitomycin C, daunorubicin, and vinblastine. The proteinaceous drugs with which the monoclonal antibodies of the invention can be labeled include immunomodulators and other biological response modifiers.

The term "biological response modifiers" is meant to encompass substances that are involved in modifying the immune response in such manner as to enhance the destruction of the antigen-bearing tumor for which the monoclonal antibodies of the invention is specific. Examples of immune response modifiers include such compounds as lymphokines. Lymphokines include tumor necrosis factor, interleukins, e.g., IL1 through IL15, lymphotoxin, macrophage activating factor (MAF), migration inhibition factor (MIF), colony stimulating factor (CSF), and interferon. Interferons with which the monoclonal antibodies of the invention can be labeled include alpha-interferon, beta-interferon and gamma-interferon and their subtypes.

In using radioisotopically conjugated monoclonal antibodies of the invention for immunotherapy, certain isotopes may be more preferable than others depending on such factors as leukocyte distribution as well as isotope stability and emission. If desired, the tumor cell distribution can be evaluated by the in vivo diagnostic techniques described above. Depending on the malignancy, some emitters may be preferable to others. In general, alpha and beta particle-emitting radioisotopes are preferred in immunotherapy. For example, if an animal has solid tumor foci, as in a carcinoma, a high energy beta emitter capable of penetrating several millimeters of tissue, such as $^{90}Y$, may be preferable. On the other hand, if the malignancy consists of simple target cells, as in the case of leukemia, a shorter range, high energy alpha emitter, such as $^{212}Bi$, may be preferable. Examples of radioisotopes which can be bound to the monoclonal antibodies of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$, and $^{188}Re$.

Lectins are proteins, usually isolated from plant material, which bind to specific sugar moieties. Many lectins are also able to agglutinate cells and stimulate lymphocytes. Ricin is a toxic lectin that has been used immunotherapeutically. This is preferably accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin (DT), a substance produced by $Corynebacterium$ $diphtheria$, can be used therapeutically. DT consists of an alpha and beta subunit which under proper conditions can be separated. The toxic alpha component can be bound to an antibody and used for site specific delivery to a cell bearing an antigen for which the monoclonal antibodies of the invention are specific. Other therapeutic agents which can be coupled to the monoclonal antibodies of the invention are known, or can be easily ascertained, by those of ordinary skill in the art.

The labeled or unlabeled monoclonal antibodies of the present invention can also be used in combination with therapeutic agents such as those described above. Especially preferred are therapeutic combinations comprising the monoclonal antibody of the invention and immunomodulators and other biological response modifiers. Thus, for example, the monoclonal antibodies of the invention can be used in combination with alpha-interferon. This treatment modality enhances monoclonal antibody targeting of carcinomas by increasing the expression of monoclonal antibody reactive antigen by the carcinoma cells (Greiner et al., 1987, $Science,$ 235:895). Alternatively, the monoclonal antibodies of this invention may be used, for example, in combination with gamma-interferon to activate and increase the expression of Fc receptors by effector cells, which, in turn, results in an enhanced binding of the monoclonal antibody to the effector cell and killing of target tumor cells. Those of skill in the art will be able to select from the various biological response modifiers to create a desired effector function which enhances the efficacy of the monoclonal antibodies of the invention.

When the monoclonal antibodies of the present invention are used in combination with various therapeutic agents, such as those described herein, the administration of the monoclonal antibody and the therapeutic agent usually occurs substantially contemporaneously. The term "substantially contemporaneously" means hat the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the tumor, the condition of the patient and the half-life of the agent.

Using the monoclonal antibodies of the present invention, it is possible to design therapies combining all of the characteristics described herein. In a given situation, it may be desirable to administer a therapeutic agent, or agents, prior to the administration of the monoclonal antibodies of the invention, in combination with effector cells and the same, or different, therapeutic agent or agents. For example, it may be desirable to treat patients with malignant disease by first administering gamma-interferon and interleukin-2 daily for 3 to 5 days, and on day 5 administer the monoclonal antibody of the invention in combination with effector cells, as well as gamma-interferon, and interleukin-2.

It is also possible to utilize liposomes with the monoclonal antibodies of the present invention in their membranes to specifically deliver the liposome to the area of the tumor expressing SCLC-specific antigens. These liposomes can be produced such that they contain, in addition to monoclonal antibody, immunotherapeutic agents, such as those described above, which would then be released at the tumor site (e.g., Wolff et al., 1984, *Biochem. et Biophys. Acta*, 802:259).

The dosage ranges for the administration of the monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days.

Generally, when the monoclonal antibodies of the present invention are administered conjugated with therapeutic agents, lower dosages, comparable to those used for in vivo immunodiagnostic imaging, can be used. The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

As mentioned above, anti-idiotypic monoclonal antibodies to the antibodies according to the present invention may be used in therapies and treatments in active tumor immunization and tumor therapy (See, S. M. Larson et al., 1986, "Therapeutic applications of radiolabeled antibodies: Current situation and prospects", *Int. J. Rad. Appl. Instrum.*, B).

The monoclonal antibodies, or binding fragments thereof, according to the present invention, may be used to quantitatively or qualitatively detect the presence of the SCLC-specific antigens as described on tumor or cancer cells. This can be achieved, for example, by immunofluorescence techniques employing a fluorescently labeled antibody, coupled with light microscopic, flow cytometric, or fluorometric detection. In addition, the antibodies, or binding fragments thereof, according to the present invention may additionally be employed histologically, as in immunofluorescence, immunoelectron microscopy, or non-immuno assays, for the in situ detection of SCLC-specific antigen on cells, such as for use in monitoring, diagnosing, or detection assays.

In situ detection may be accomplished by removing a histological specimen from a patient, and applying thereto a labeled antibody according to this invention. The antibody, or antigen-binding fragment thereof, is preferably applied by overlaying the labeled antibody or fragment onto the biological sample. Through the use of such a procedure, it is possible to determine not only the presence of the SCLC antigen, or conserved variants, or peptide fragments, but also its distribution in the examined tissue. Those having skill in the art will readily recognize that any of a wide variety of histological methods, e.g., staining procedures, can be modified in order to achieve such in situ detection.

Immunoassay and non-immuno assays for SCLC antigen, or conserved variants, or peptide fragments thereof, typically comprise incubating a sample, such as a biological fluid, tissue extract, freshly harvested cells, or lysates of cells that have been incubated in cell culture, in the presence of a detectably-labeled antibody that recognizes the SCLC antigen, conserved variants, or peptide fragments thereof, such as the SCLC-specific monoclonal antibodies, or binding fragments thereof, of the present invention. Thereafter, the bound antibody, or binding fragment thereof, is detected by a number of techniques well known in the art.

The biological sample may be brought into contact with, and immobilized onto, a solid phase support or carrier, such as nitrocellulose, or other solid support or matrix, which is capable of immobilizing cells, cell particles, membranes, or soluble proteins. The support may then be washed with suitable buffers, followed by treatment with the detectably-labeled anti-SCLC antibody. The solid phase support may then be washed with buffer a second time to remove unbound antibody. The amount of bound label on the solid support may then be detected by conventional means. Accordingly, in another embodiment of the present invention, compositions are provided comprising the monoclonal antibodies, or binding fragments thereof, bound to a solid phase support, such as described herein.

By solid phase support or carrier or matrix is meant any support capable of binding an antigen or an antibody. Well-known supports or carriers include glass, plastic, nylon wool, polystyrene, polyethylene, polypropylene, dextran, nylon, amylases, films, resins, natural and modified celluloses, polyacrylamides, agarose, alumina gels, gabbros, and magnetite. The nature of the carrier can be either soluble to some extent, or insoluble for the purposes of the present invention. The support material may have virtually any possible structural configuration as long as the coupled molecule is capable of binding to an antigen or antibody. Thus, the support configuration may be spherical, as in a bead, cylindrical, as in the inside surface of a test tube, or the external surface of a rod. Alternatively, the surface may be flat, such as a sheet, film, test strip, stick, and the like. In addition, the solid support is preferably inert to the reaction conditions for binding and may have reactive groups, or activated groups, in order to attach the monoclonal antibody, a binding fragment, or the binding partner of the antibody. The solid phase support may also be useful as a chromatographic support, such as the carbohydrate polymers Sepharose®, Sephadex®, or agarose. Indeed, a large number of such supports for binding antibody or antigen are commercially available and known to those having skill in the art.

The binding activity for a given anti-SCLC antibody may be determined by well-known methods. Those skilled in the art will be able to determine operative and optimal assay conditions for each determination by employing routine experimentation.

With respect to the anti-SCLC antibodies, numerous ways to detectably label such protein molecules are known and practiced in the art. For example, one way the antibodies can be detectably labeled is by linking the antibody to an enzyme, e.g., for use in an enzyme immunoassay (EIA), (A. Voller et al., 1978, "The Enzyme Linked Immunosorbent Assay (ELISA)", *Diagnostic Horizons*, 2:1–7;, *Microbiological Associates Quarterly Publication*, Walkersville, Md.; A. Voller et al., 1978, *J. Clin. Pathol.*, 31:507–520; J. E. Butler et al., 1981, *Meths. Enzymol.*, 73:482–523; *Enzyme Immunoassay*, 1980, (Ed.) E. Maggio, CRC Press, Boca Raton, Fla.; *Enzyme Immunoassay*, 1981, (Eds.) E. Ishikawa et al., Kgaku Shoin, Tokyo, Japan). The enzyme that is bound to the antibody reacts with an appropriate substrate, preferably a chromogenic substrate, so as to produce a chemical moiety which can be detected, for example, by spectrophotometric, fluorometric, or by visual detection means. Nonlimiting examples of enzymes which can be used to detectably label the antibodies include malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, ribonuclease, urease, catalase, glucose-6-phosphate dehydrogenase, glucoamylase and acetylcholinesterase. The detection can be accomplished by calorimetric methods, which employ a chromogenic substrate for the enzyme, or by visual comparison of the extent of enzymatic reaction of a substrate compared with similarly prepared standards or controls.

A variety of other immunoassays may also be used for detection. For example, by labeling the antibodies, or binding fragments thereof, with a radioisotope, a radioimmunoassay (RIA) can be used to detect SCLC-specific antigens (e.g., B. Weintraub, "Principles of Radioimmunoassays", *Seventh Training Course on Radioligand Techniques*, The Endocrine Society, March, 1986). The radioactive isotope label can be detected by using a gamma counter or a scintillation counter or by radiography.

The antibodies, or their antigen-binding fragments can also be labeled using a fluorescent compound. When the fluorescently labeled antibody is exposed to light of the proper wavelength, its presence can then be detected due to fluorescence. Among the most commonly used fluorescent labeling compounds are, without limitation, fluorescein isothiocyanate, rhodamine, phycoerythrin, phycocyanin, allophycocyanin, o-phthaldehyde and fluorescamine. Detectably labeled fluorescence-emitting metals, such as $^{152}$Eu, or others of the lanthanide series, can be used to label the antibodies, or their binding fragments, for subsequent detection. The metals can be coupled to the antibodies via such metal chelating groups as diethylenetriaminepentacetic acid (DTPA), or ethylenediaminetetraacetic acid (EDTA).

The antibodies can also be detectably labeled by coupling them to a chemiluminescent compound. The presence of the chemiluminescent-tagged antibody is then determined by detecting the presence of luminescence that develops during the course of a chemical reaction. Examples of particularly useful chemiluminescent labeling compounds include, without limitation, luminol, isoluminol, theromatic acridinium ester, imidazole, acridinium salt and oxalate ester. Similarly, a bioluminescent compound may be used to label the antibodies of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent labeling compounds include luciferin, luciferase and aequorin.

Another embodiment of the present invention provides diagnostics, diagnostic methods and imaging methods for SCLC cancers and tumors using the monoclonal antibodies and binding fragments thereof as described by the present invention. The diagnostic uses of the antibodies according to the present invention embrace primary tumors and cancers, as well as metastases. Other cancers and tumors bearing the surface antigens discovered on SCLC cells, bindable by the monoclonal antibodies, or binding fragments thereof, of this invention, and described herein are also amenable to these diagnostic and imaging procedures.

A diagnostic method according to the invention comprises administering, introducing, or infusing the monoclonal antibodies or their binding fragments as described herein, with or without conjugation to a detectable moiety, such as a radioisotope. After administration or infusion, the antibody or binding fragment binds to the tumor or cancer cells, after which the location of the bound antibodies or fragments is detected. For detectably labeled antibodies or fragments, for example, those labeled with a radioisotope, imaging instrumentation may be used to identify the location of the agent within the body. For unlabeled antibodies or fragments, a second detectable reagent may be administered, which locates the bound antibodies or fragments so that they can be suitable detected. Similar methods have been employed for other antibodies, and the skilled practitioner will be aware of the various methods suitable for imaging the location of detectably bound antibodies or fragments within the body. As a nonlimiting guide, about 10–1000 μg, preferably about 50–500 μg, more preferably about 100–300 μg, most preferably about 200–300 μg of Protein G-purified MoAb are administered. For mice, for example, using 200 μg MoAb and intraperitoneal (i.p.) administration, MoAb is injected three times a week for three weeks. For 300 μg MoAb and intraperitoneal (i.p.) administration, MoAb is injected two times a week for three weeks. Applicable doses for humans include about 100–200 mcg/kg, or 350–700 mg/m$^2$.

It is to be further understood that a cocktail of different monoclonal antibodies, such as a mixture of the specific monoclonal antibodies described herein, or their binding fragments, may be administered, if necessary or desired, to alleviate SCLC. Indeed, using a mixture of monoclonal antibodies, or binding fragments thereof, in a cocktail to target several antigens, or different epitopes, on cancer cells, is an advantageous approach, particularly to prevent evasion of tumor cells and/or cancer cells due to downregulation of one of the antigens.

In another embodiment, the present invention assists in the diagnosis of cancers and tumors by the identification and measurement of shed SCLC cell surface glycoprotein in body fluids, such as blood, serum, plasma, sputum and the like. For those cancers that express the surface antigens described herein, wherein the antigens are recognized by and immunoreactive with the monoclonal antibodies and their binding fragments according to the present invention, the ability to detect antigens that are shed or sloughed off from the cancer or tumor cells provides a needed means of early diagnosis, thereby affording the opportunity for early treatment. Early detection is especially important for those cancers that are difficult to diagnose in their early stages. Measurement of shed surface glycoprotein in a whole blood sample, for example, by the use of one or more of the antibodies or their binding fragments according to this invention provides early detection, diagnosis and immediate intervention and/or treatment for the evasive cancer or tumor. Treatment may comprise antibody-based immunotherapy as described above, in combination with other immunomodulatory agents, if necessary or desired.

Moreover, the level of shed antigen that is detected and measured in a body fluid sample such as blood provides a means for monitoring the course of therapy for the cancer or tumor, including, but not limited to, surgery, chemotherapy, radiation therapy, the therapeutic methods of the present invention, and combinations thereof. By correlating the level of SCLC-specific antigen in the body fluid with the severity of disease, the level of such antigen can be used to indicate successful removal of the primary tumor, cancer, and/or metastases, for example, as well as to indicate and/or monitor the effectiveness of other therapies over time. For example, a decrease in the level of the cancer or tumor-specific antigen over time indicates a reduced tumor burden in the patient. By contrast, no change, or an increase, in the level of antigen over time indicates ineffectiveness of therapy, or the continued growth of the tumor or cancer.

In a related embodiment, the present invention provides methods for diagnosing the presence of SCLC by assaying for changes of levels in the SCLC cell surface antigens in cells, tissues or body fluids compared with the levels in cells, tissues, or body fluids, preferably of the same type, from normal human controls. A change in levels of antigen in the patient versus the normal human control is associated with the presence of SCLC. Without limiting this aspect of the present invention, typically, for a quantitative diagnostic assay, a positive result indicating that the patient being tested has cancer, is one in which levels of the SCLC antigen in or on cells, tissues or body fluid are at least two times higher, and preferably three to five times higher, or greater, than the levels of the antigens in or on the same cells, tissues, or body fluid of the normal individual as control. Normal controls include a human without cancer and/or non-cancerous samples from the patient.

Another embodiment of the present invention relates to pharmaceutical compositions comprising one or more monoclonal antibodies, or binding fragments thereof, according to the invention, together with a physiologically- and/or pharmaceutically-acceptable carrier, excipient, or diluent. The antibodies, or binding fragments, specifically recognize an SCLC-epitope on one or more SCLC cell surface antigens and bind to the antigens. The SCLC-specific cell surface antigens are further characterized as described herein and above.

More specifically, the present invention is directed to pharmaceutical compositions comprising a monoclonal antibody, or binding fragment thereof, including the monoclonal antibodies produced from the hybridoma cell lines deposited at the American Type Culture Collection having ATCC Accession Nos. PTA-2357, PTA-2358, PTA-2359 and PTA-2360; antibodies that are capable of binding to the same antigenic determinant as do the monoclonal antibodies produced by the hybridoma cell lines deposited at the American Type Culture Collection and having ATCC Accession Nos. PTA-2357, PTA-2358, PTA-2359 and PTA-2360; binding fragments of the hybridoma cell lines deposited at the American Type Culture Collection and having ATCC Accession Nos. PTA-2357, PTA-2358, PTA-2359 and PTA-2360; and binding fragments of monoclonal antibody capable of binding to the same antigenic determinant as do the monoclonal antibodies produced by the hybridoma cell lines deposited at the American Type Culture Collection and having ATCC Accession No. PTA-2357, PTA-2358, PTA-2359 and PTA-2360; and a pharmaceutically-acceptable carrier or diluent. Antibody fragments include but are not limited to F(ab')$_2$ fragments, F(ab) fragments, fragments produced by an F(ab) expression library, Fv fragments, Fd' fragments, or Fd fragments.

Preferably, the antibodies or binding fragments thereof are delivered parenterally, such as by intravenous, subcutaneous, or intraperitoneal administration, e.g., injection. Suitable buffers, carriers, and other components known to the art can be used in formulating a composition comprising the antibody or fragments for suitable shelf-life and compatibility with administration. These substances may include ancillary agents such as buffering agents and protein stabilizing agents (e.g., polysaccharides).

More specifically, therapeutic formulations of the antibodies, or binding fragments thereof, are prepared for storage by mixing the antibodies or their binding fragments, having the desired degree of purity, with optional physiologically acceptable carriers, excipients, or stabilizers (Remington's Pharmaceutical Sciences, 17th edition, (Ed.) A. Osol, Mack Publishing Company, Easton, Pa., 1985), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The antibodies, or binding fragments thereof, also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

Antibodies or their binding fragments to be used for in vivo administration must be sterile. This is readily accomplished by filtration through sterile filtration membranes, prior to or following lyophilization and reconstitution. The antibodies, or binding fragments thereof, ordinarily will be stored in lyophilized form or in solution.

Therapeutic antibody compositions generally are placed into a container having a sterile access port, for example, an intravenous solution bag or vial having a stopper pierceable by a hypodermic injection needle. The route of administration of the antibodies, or binding fragments thereof, in accordance with the present invention, is in accord with known methods, e.g., injection or infusion by intravenous, intraperitoneal, intramuscular, intraarterial, subcutaneous, intralesional routes, by aerosol or intranasal routes, or by sustained release systems as noted below. The antibodies, or binding fragments thereof, are administered continuously by infusion or by bolus injection. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., 1981, *J. Biomed. Mater. Res.*, 15:167–277 and Langer, 1982, *Chem. Tech.*, 12:98–105), or poly(vinylalcohol)], polylactides (U.S. Pat. No. 3,773,919; EP 58,481), copolymers of L-glutamic acid and gamma ethyl-L-glutamate (Sidman et al., 1983, *Biopolymers*, 22:547–556), non-degradable ethylene-vinyl acetate (Langer et al., supra), degradable lactic acid-glycolic acid copolymers such as the LUPRON DEPOT.TM. (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in effectiveness. Rational strategies can be devised for antibody stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release antibody compositions also include liposomally entrapped antibodies, or their binding fragments. Liposomes containing the antibodies are prepared by known methods, for example, DE 3,218,121; Epstein et al., 1985, *Proc. Natl. Acad. Sci. USA*, 82:3688–3692; Hwang et al., 1980, *Proc. Natl. Acad. Sci. USA*, 77:4030–4034; EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal antibody therapy.

An effective amount of antibody to be employed therapeutically will depend, for example, upon the therapeutic and treatment objectives, the route of administration, the age, condition, and body mass of the patient undergoing treatment or therapy, and auxiliary or adjuvant therapies being provided to the patient. Accordingly, it will be necessary and routine for the practitioner to titer the dosage and modify the route of administration, as required, to obtain the optimal therapeutic effect. A typical daily dosage might range from about 1 mg/kg to up to about 100 mg/kg or more, preferably from about 1 to about 10 mg/kg/day depending on the above-mentioned factors. Typically, the clinician will administer antibody until a dosage is reached that achieves the desired effect. The progress of this therapy is easily monitored by conventional assays.

Various adjuvants may be used to increase the immunological response to the SCLC antigen and to elicit specific anti-SCLC antibodies according to the present invention. Depending on the host species to be immunized, adjuvants may include, but are not limited to, Freund's (complete and incomplete), mineral gels, such as aluminum hydroxide, surface active agents, such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

The antibodies of the present invention are also useful for in vitro diagnostic applications for the detection of human SCLC cells, or neuroendocrine cells, e.g., neuroblastoma, that possess the antigen for which the antibodies are specific. As detailed above, in vitro diagnostic methods include immunohistological or immunohistochemical detection of tumor cells (e.g., on human tissue, or on cells dissociated from excised tumor specimens), or serological detection of tumor associated antigens (e.g., in blood samples or other biological fluids). Immunohistochemical techniques involve staining a biological specimen, such as a tissue specimen, with one or more of the antibodies of the invention and then detecting the presence on the specimen of antibody-antigen complexes comprising antibodies bound to the cognate antigen. The formation of such antibody-antigen complexes with the specimen indicates the presence of SCLC in the tissue.

Detection of the antibody on the specimen can be accomplished using techniques known in the art such as immunoenzymatic techniques, e.g., immunoperoxidase staining technique, or the avidin-biotin technique, or immunofluorescence techniques (see, e.g., Ciocca et al., 1986, "Immunohistochemical Techniques Using Monoclonal Antibodies", *Meth. Enzymol.*, 121:562–79 and *Introduction to Immunology*, Ed. Kimball, ($2^{nd}$ Ed), Macmillan Publishing Company, 1986, pp. 113–117). Serologic diagnostic techniques involve the detection and quantification of tumor-associated antigens that have been secreted or 'shed' into the serum or other biological fluids of patients thought to be suffering from SCLC, as mentioned hereinabove. Such antigens can be detected in the body fluids using techniques known in the art, such as radioimmunoassays (RIA) or enzyme-linked immunoabsorbant assays (ELISA), wherein antibody reactive with the shed antigen is used to detect the presence of the antigen in a fluid sample (See, e.g., Uotila et al., 1981, *J. Immunol. Methods*, 42:11 and S. T. Fayed et al., 1998, *Disease Markers*, 14(3):155–160). Detection of the shed SCLC antigen is carried out as described above.

In yet a further aspect of the invention, monoclonal antibodies or binding fragments to the SCLC surface glycoprotein are provided labeled with a detectable moiety, such that they may be packaged and used, for example, in kits, to diagnose or identify cells having the aforementioned antigen. The kits preferably contain an instruction manual for use of the kit. Non-limiting examples of such labels include fluorophores such as fluorescein isothiocyanate; chromophores, radionuclides, or enzymes. Such labeled antibodies or binding fragments may be used for the histological localization of the antigen, ELISA, cell sorting, as well as other immunological techniques for detecting or quantifying the antigen, and cells bearing the antigen, for example.

The anti-SCLC antibodies of the present invention exhibit a narrow tumor specificity. In this regard, representative MoAb 109.12 reacted with human SCLC antigen but not with human neuroendocrine antigens, human (non-SCLC) lung, human multiple myeloma tissue, human ovarian tissues (fresh ovarian tissue and cell line), human chronic myelogenous leukemia tissue, and a human B cell tumor. However, the SCLC-specific MoAbs were found to immunoreact with cells from a human pancreatic cancer and exhibited a distinct pattern of reactivity (FIGS. 6A and 6B). In this regard, cell lines from various human cancerous tissues or cell lines were tested for binding to the monoclonal antibodies according to the present invention.

The results of experiments in which the 109.12 and 51.2 MoAbs served as representative antibodies demonstrated that of three pancreatic tumors tested, two that reacted with the monoclonal antibodies exhibited a different pattern of reactivity, and the antibodies also bound to cell surface antigens of distinct MW (i.e., an ~200 kDa antigen, as well as an antigen of 79–120 kDa on the pancreatic cancer, versus the single antigen of ~200 KDa on the SCLC cells). Moreover, the SCLC-specific MoAbs did not react with human B cell tumors (IM9 and HT), human breast tissues (fresh breast tissue and cell line) and human prostate tissue. According to this invention, the SCLC-specific MoAbs immunoreact with different epitopes of the same antigen on pancreatic cancer cells and exhibit narrow tumor specificity.

Characterization of the SCLC 200 KDa surface antigen shows that this antigen is detected by MoAbs 51.2, 109.12 and 37.14 as a single band by Western Blot analysis (see, for example, FIG. 8B using representative MoAb 109.12). That the approximately 200 KDa antigen is an integral membrane protein is reflected by its remaining intact following boiling (5 minutes), solubilization with the nonionic detergent IGEPAL® (Sigma, St. Louis, Mo.) and solubilization with SDS. After immunoaffinity purification of the IGEPAL®-solubilized portion of the antigen on a CN-Br-activated Sepharose column coupled to the 109.12 monoclonal antibody, the 200 KDa antigen comprises two bands, both of which are between about 75 and 120 MW in size.

Figure 7A:
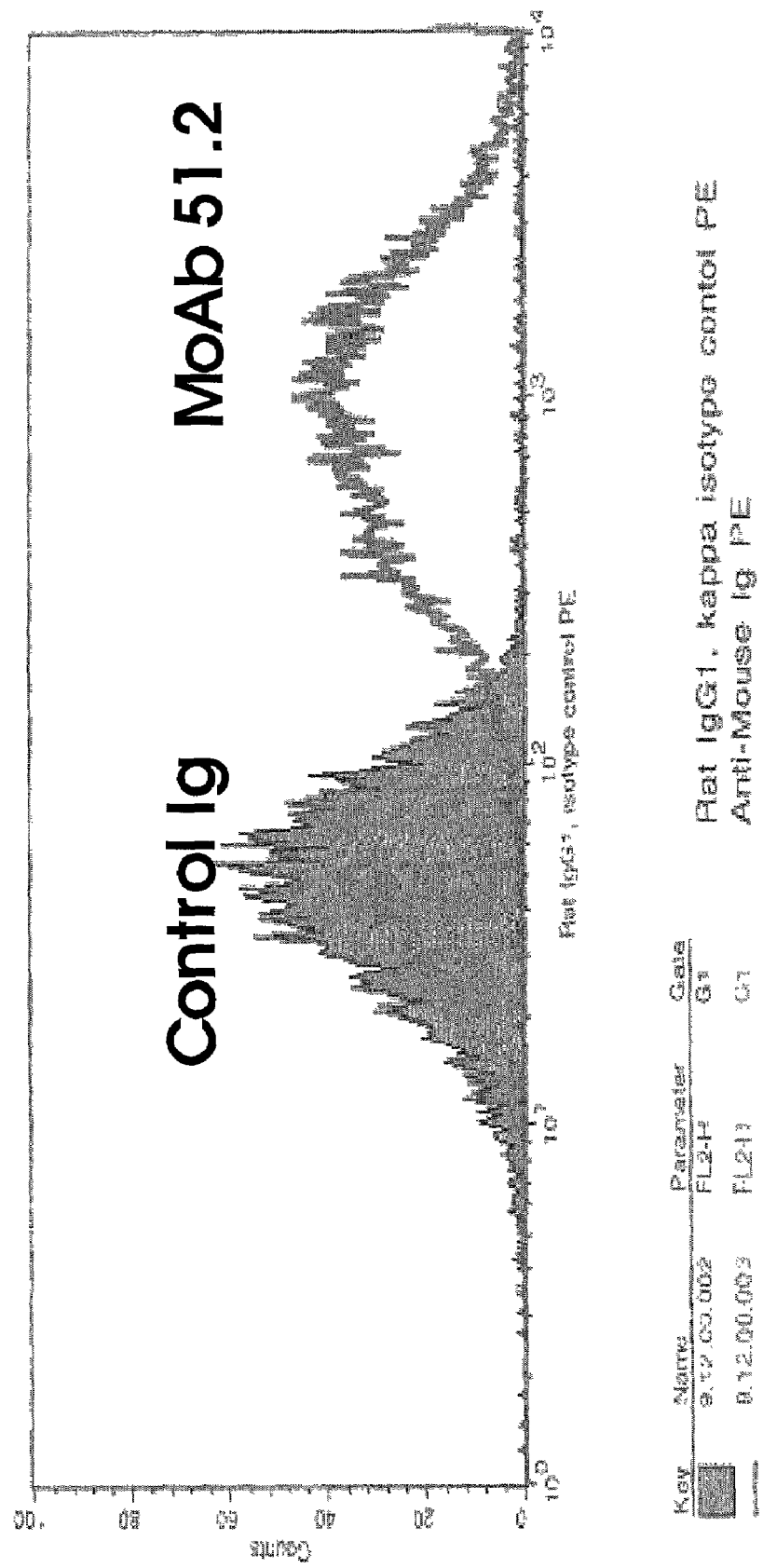
FIGS. 7A and 7B present the results of internalization studies using MoAb 51.2 of the present invention.
Figure 7B:
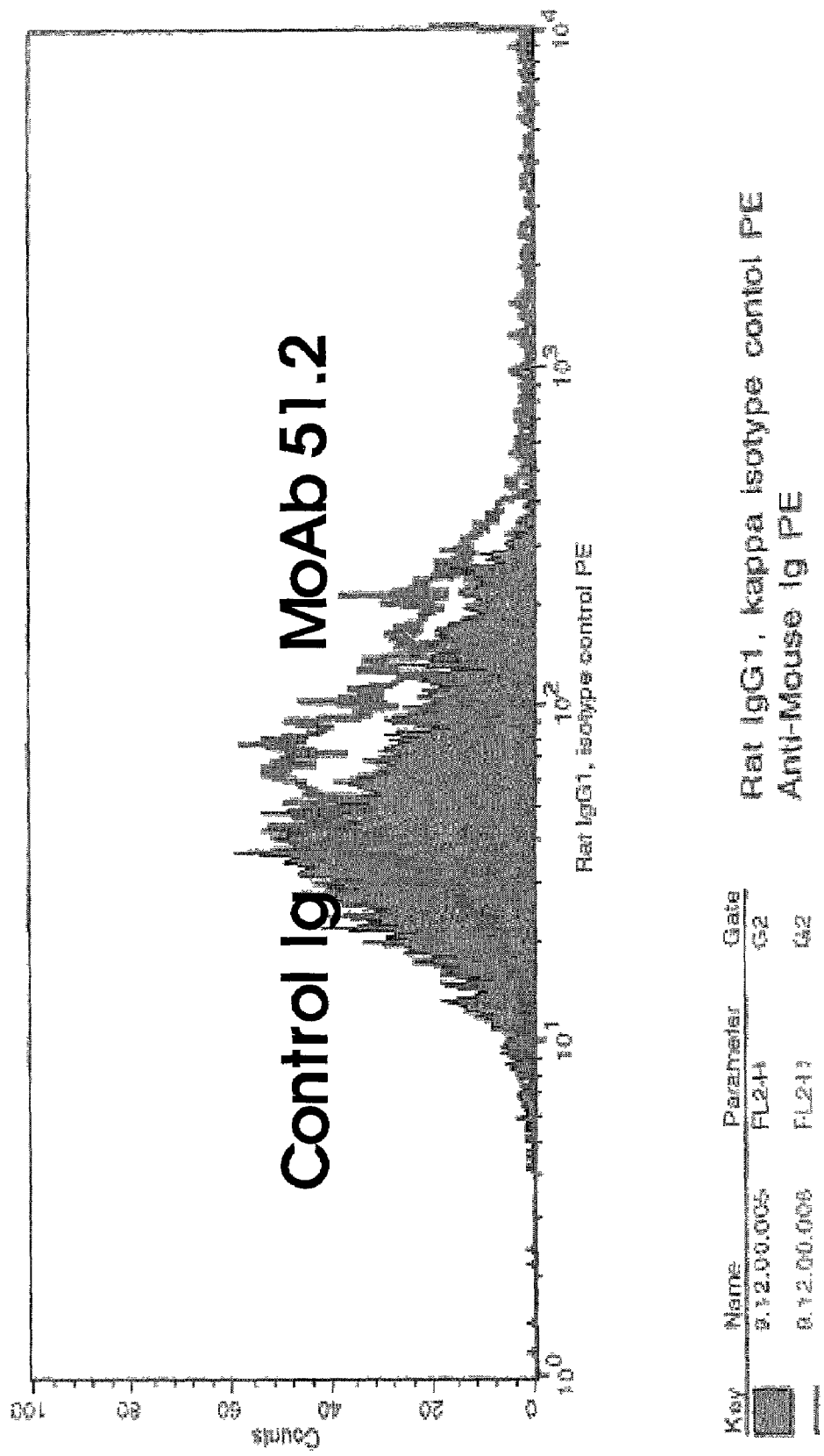

In internalization studies (FIGS. 7A and 7B), the MoAb 51.2 was shown to internalize into human SCLC cells, but not to internalize into cells of a human neuroendocrine cancer cell line. Such findings have a direct bearing on the target specificity of the monoclonal antibodies described herein. The internalization results indicate that the antibody(ies) can be conjugated to toxins, which upon binding of the antibody(ies) to the cancerous cells, will deliver the toxin inside the cells and thus will eradicate the cells without compromising the cells and tissue in the vicinity. The internalization parallels the binding attributes of the MoAbs, e.g., 51.2, and underscores the high specificity of the antibodies, particularly the 51.2 MoAb for SCLC cells.

EXAMPLES

The examples as set forth herein are meant to exemplify the various aspects of carrying out the invention and are not intended to limit the invention in any way.

Example 1

Materials And Methods

Sources of Cells:

Cells and cell lines utilized and evaluated in the experiments described were purchased from the American Type Culture Collection (ATCC), 10801 University Boulevard, Manassas, Va. 20110-2209. Specifically, the cell lines include human SCLC cell lines, i.e., DMS114 (ATCC No. CRL-2066), NCI-H209 (ATCC No. HTB-172), NCI-H510A (ATCC No. HTB-184); neuroendocrine cell lines, i.e., SK-N-AS (ATCC No. CRL-2137), Be(2)-/M17 (ATCC No. CRL-2267), MC-IXC (ATCC No. CRL-2270); LnCap (prostate cancer cell line, ATCC No. CRL-1740); Caski (cervical cancer cell line, ATCC No. 1550); Namalwa (EBV-transformed tumor cell line, ATCC No. CRL-1432); HT (ATCC No. CRL-2260); IM9 (ATCC No. CCL-159); human myeloma cell lines (U266, OPM, RPMI-1860, KR12 and NCI H929); neuroblastoma cell line (NCI H2106); and the chronic myelogenous leukemic cell line K562 (ATCC No. CCL-243). Fresh clinical specimens such as breast cancer, liver carcinoma, ovarian cancer, cervical cancers were obtained from Stanford University Hospital (CA) or NDRI (MD).

Preparation Of Cell Membranes:

Cells were lysed following 3 repeated cycles of freeze-thaw. Membranes were prepared from cell lysates following a 30 minute centrifugation at 2500 rpm. The supernatant, which contained cytosolic protein and membranes, was further separated by centrifugation at 40,000 rpm. Pellets containing the membrane fractions were collected and stored at −20° C.

For detergent extraction of membrane proteins, cell membranes at a concentration of approximately 10 mg/ml were diluted 1:1 in IGEPAL® CA-630 (a nonionic detergent formerly known as Nonidet P-40), at 0.312% in PBS (final detergent concentration of 0.156%) and incubated on ice for 1 hour. The preparations were centrifuged for 1 hour at 4° C. at 16,000×g. The soluble portion (supernatant) was subjected to SDS-PAGE and detected with MoAb by Western Blot (see FIG. 8B).

Mice and Immunization:

Balb/c and SCID (6–8 week old female) mice were purchased from Taconic (NY). Mice were immunized with a pool of human SCLC cells (i.e., DMS114, NCI-H209 and NCI-H510A). About $5 \times 10^5 - 5 \times 10^6$ total cells (in 50 μl containing Ribi adjuvant, 50% v/v) were injected into the right footpad. In the left footpad, mice were injected with a pool of human neuroendocrine cell lines (SKON-AS, MC-IXC and Be(2)-/M17), in 50 μl containing Ribi adjuvant, 50% v/v). The mice were boosted 14 days later with a pool of SCLC cells ($5 \times 10^4 - 5 \times 10^5$ total). The right popliteal lymph node was removed and the extracted cells were fused with murine myeloma Sp2/0 cells three days after the second immunization.

Generation of B Cell Hybridomas:

Monoclonal antibodies specific to SCLC were produced by conventional methods. Spleen cells were fused with murine myeloma sp2/0 and seeded into 96 well-plates at a final concentration of $1 \times 10^4$ cells/well.

Cellular ELISA:

Supernatants from hybridoma cultures were screened for direct binding to membrane preparations extracted from a pool of SCLC cell lines and compared with background binding to control neuroendocrine cell lines, using an ELISA assay. SCLC and neuroendocrine cells ($1 \times 10^5$ cells/well) were dispensed into a 96-well tissue culture plate (Costar, Cambridge, Mass.) and incubated with hybridoma supernatant (50 μl/well) for 30 minutes at room temperature (RT). The cells were then washed three times with phosphate buffered saline, pH 7.4 (PBS), (Gibco BRL). Next, biotinylated rabbit anti-mouse (gamma) solution (0.5 μg/ml) was added to the wells (50 μg per well). Following a 1-hour of incubation and extensive washes as above, streptavidin-conjugated horseradish peroxidase (Zymed, CA), diluted to 1:10,000 in blocking buffer, was added to the wells and a 30-minute incubation followed. Substrate was added (100 µl/well of tetramethylbenzidine (DAKO Corporation, California) and the plates were incubated for 30 minutes at RT. The reaction was stopped using 100 µl/well of 2N $H_2SO_4$. The plates were read using an automated ELISA Plate Reader at a wavelength of 450 nm.

Gel Electrophoresis and Western Blotting:

SDS-polyacrylamide gels (8%) were prepared according to standard protocols and used for Western blotting. Membrane preparations or homogenates (50 µg/lane) (e.g., tumor cells lines, fresh normal human tissues, and freshly excised human tumors) were loaded onto the above SDS gels and fractionated. Blots were incubated in a blocking buffer containing 10% BSA in TBST buffer (20 mM Tris-base, 137 mM NaCl {pH 7.6}, and 0.05% Tween 20) for 1-hour, followed by incubation in the primary MoAb (0.1 µg/ml) for 1–2 hours. After washing 3 times in TBST buffer, blots were incubated for 30 minutes with a horse radish peroxidase (HRP)-conjugated secondary antibody (0.05 µg/ml). The blots were developed with the ECL™ (Amersham Pharmacia Biotech, Piscataway, N.J.) Western Blot chemiluminescent detection reagent according to the manufacturer's instructions.

Evaluation of Carbohydrates in Glycoprotein(s) Recognized by SCLC-specific MoAbs:

Blots of membranes from SCLC prepared as described above are tested with a panel of lectins (e.g., WGA, *Triticum vulgar* or wheat germ; PNA, *Arachis hypogaea* or peanut; BPA, *Bauhinia purpurea* or camel's foot tree; SBA, *Glycine max* or soybean; MPA, *Maclura pomifera* or osage orange; UEA-I, *Ulex europaeus* or gorse; and ConA, *Concanavalia ensiformis* or jack bean) to determine the presence of specific sugar residues. As an alternative, radiolabeled lysates are preabsorbed with various lectin-agarose beads (Vector Labs, Burlingame, Calif.), and then incubated with the monoclonal antibodies of the present invention. The antigen (bound to the MoAbs) is immunoprecipitated by incubation of the supernatant with beads coated with anti-mouse Ig, and then fractionated by SDS-PAGE. Elimination of the antigen from the immunoprecipitated material will indicate that the antigen binds to the pre-clearing lectin and therefore expresses the respective sugar specificity.

Another alternative protocol for carbohydrate identification involves the inhibition of monoclonal antibody binding to antigen through competition with lectin-specific antibodies. The lectin-specific antibodies are available in either a non-conjugated form or conjugated to biotin or to fluorescein. The choice availability allows performance of the assay using various methods. Commercial kits (Vector Labs) containing the lectins and their controls are available. The lectin screening kits are designed to provide the investigator with a panel of seven lectins or lectin conjugates. The lectins have been selected to offer a variety of sugar specificities and are of the same high quality as the reagents offered individually.

Complement-Mediated Cytotoxicity:

Tumor cells are incubated in RPMI+10% FBS at $1\times10^5$ cells/well in 96 well plates. Protein-G purified SCLC-specific MoAbs or isotype control antibody are added at 1 µg/ml to 10 µg/ml in the presence of human complement for 1 hour at 37° C. and 5% $CO_2$. Controls plates contain tumor cells incubated with antibody alone, complement alone, 1% SDS, complete medium alone, and 2 µg/ml of PHA. Plates are pulsed with 1 µCi/well of $^3$H-Thymidine (Dupont-NEN) for 12–16 hours at 37° C., harvested and read on a Wallac Trilux MicroBeta counter. Percent lysis is calculated as: 100−{[mean counts/mean spontaneous proliferation (CM)]×100}. An adjusted percent lysis is calculated as [Mean percent lysis/mean maximum lysis]×100.

In Vivo Eradication of Tumor Cells:

SCLC or control tumor cells are injected intraperitoneally (i.p.) into C.B-17 SCID beige mice (Taconic, N.Y.). Each mouse receives $1\times10^6$ cells washed and resuspended in PBS. After ten days, the mice are injected i.p. with 200 µg Protein-G purified, SCLC-specific MoAbs, or isotype-matched control antibody, 3 times a week for 3 weeks. Mice incapacitated by the large tumor are euthanized. Mice are monitored for ascites growth and results are plotted as a percentage of survival.

Internalization of Antibody:

Studies are conducted to measure the internalization of MoAbs within SCLC cells. The MoAbs are conjugated to the ricin A chain toxin to form an immunotoxin. Internalization will be assessed by determining to what extent the cancer cells are killed by ricin A chain toxin (U.S. Pat. No. 5,491,088 to I. Hellstrom et al., issued Feb. 13, 1996).

Example 2

Positive Hybridomas Produce Monoclonal Antibodies that Specifically Bind to SCLC B cell hybridomas established from immunized mice as described in Example 1 were screened by cellular ELISA with a pool of human SCLC cell lines (i.e., DMS 114, NCI-H209, NCI-H510A) compared with a pool of human neuroendocrine cell lines (SK-N-AS, MC-IXC, Be (2)-M17). Eleven hybridomas out of a pool of 170 were selected based on their production of monoclonal antibodies having the ability to specifically bind to SCLC. Limiting dilution cultures (1 cell per well) were set in up in order to establish clonal B cell hybridomas. The resultant sub-clones were screened as described above. Twelve representative sub-clones exhibiting the highest mean values for absorbance against the SCLC cells were selected for further testing. Values were adjusted by subtracting the mean O.D. of the neuroendocrine cells from the SCLC cells (FIG. 1). The selected monoclonal antibody-producing B cell hybridomas were isotyped to establish the Ig gene usage (i.e., immunoglobulin isotype of the produced antibody) as well as to validate clonality of the sub-cloned hybridoma.

Example 3

MoAbs React with Antigens Present in the Cell Membranes of SCLC

The selected panel of monoclonal antibodies was tested by FACS for staining of SCLC cells compared with control (neuroendocrine or multiple myeloma) cell lines. Four MoAbs, 26.1, 141.7, 92.7, and 37.14, exhibited a stronger staining of SCLC cells, when compared with the control cell lines. Western blotting performed under reducing conditions was used to further elucidate the specificity of the selected MoAbs. MoAbs 51.2 and 109.12 detected an antigen with a MW of about 200 KDa in the lanes containing the pool of SCLC cell lines (DMS114, NCI-H209, and NCI-H510A), (FIGS. 2 and 3). The appearance of a single fuzzy band indicates that the molecule recognized by the MoAbs is a single chain glycoprotein.

The control cell membrane preparations isolated from a pool of neuroendocrine (SK-N-AS, MC-IXC, and Be (2)-M17) and multiple myeloma (RPMI 8226 and U266) cell lines, respectively, were not stained by the MoAb 109.12. A significantly fainter band appeared in the neuroendocrine lane and was absent in the MM lane for the MoAb 51.2. This observation may indicate that the recognized SCLC antigen is over-amplified in the SCLC cells, compared with the closely related neuroendocrine cells. The antigen does not seem to be expressed by MM cells, which are more developmentally distant from the SCLC cells.

Figure 4:
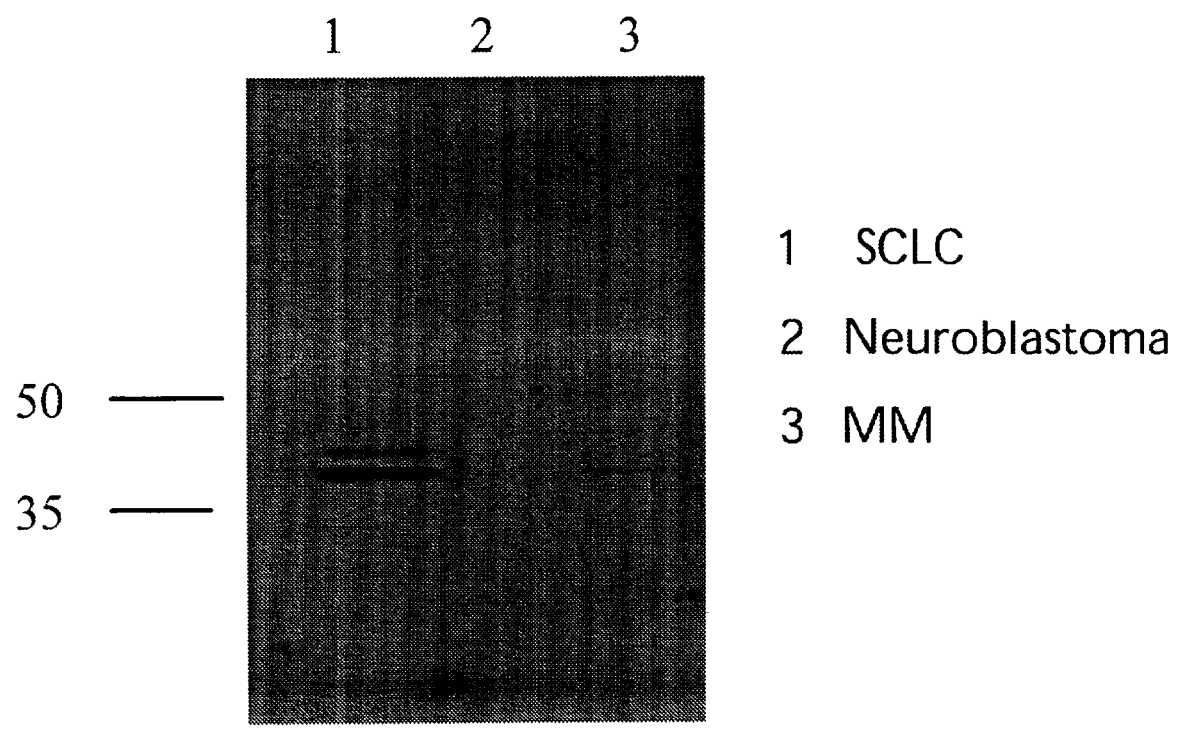
FIG. 4 shows the results of a scan of a Western Blot performed under reducing conditions to assess the specificity of the monoclonal antibody 37.14 (MoAb 37.14) for SCLC antigen. All lanes contained an equal total concentration of membrane preparation from the designated cell lines. Lane 1: SCLC cell membranes; lane 2: neuroblastoma cell membranes; lane 3: multiple myeloma (MM) cell membranes.
Figure 5:
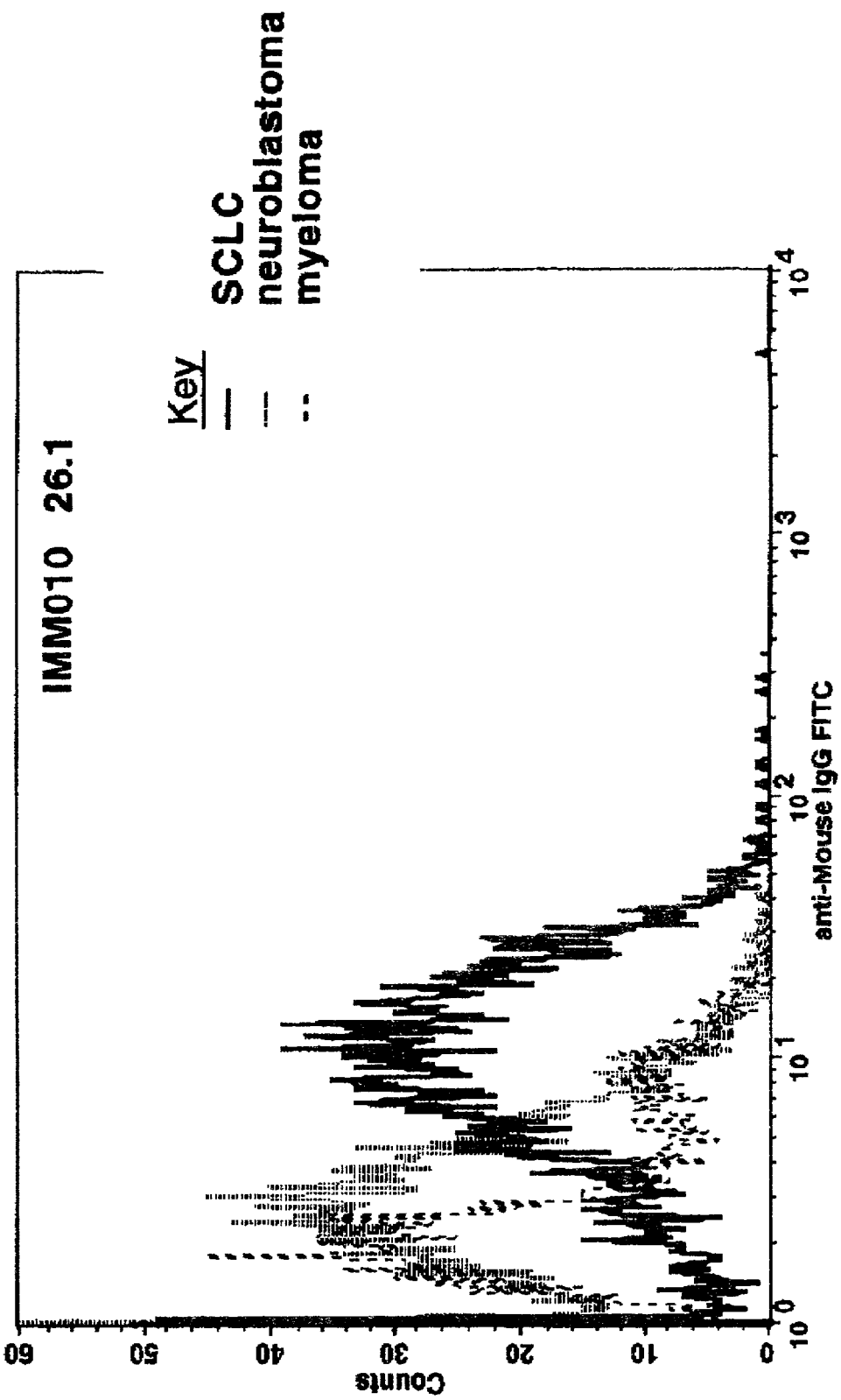
FIG. 5 shows a fluorescence activated cell sorter (FACS) analysis of the reactivity of the SCLC-specific monoclonal antibody 26.1, generated according to the present invention, against antigens present on SCLC cells, neuroblastoma cells and multiple myeloma cells. Supernatant containing monoclonal antibody from the (IMM010) 26.1 hybridoma clone was assayed for antibody reactivity with the various cell types. A fluorescein isothiocyanate (FITC)-labeled anti-mouse IgG was used to detect the presence of MAb 21.6 bound to cells.

Monoclonal antibody 37.14 reacted with an antigen having a lower molecular weight (between 35–50 kDa). The latter antigen appeared to comprise two fragments or chains, which are closely related in their mass (FIG. 4). Interestingly, MoAb 26.1 plainly recognized a SCLC-specific cell surface molecule, but failed to react with SCLC membranes in a Western Blot performed under reducing conditions. This result may indicate that the epitope recognized by MoAb 26.1 is a conformational epitope, which is destroyed by linearization treatment in the presence of SDS.

Example 4

Immunohistochemical Analysis

For the immunohistochemical analyses performed on normal human lung tissue and SCLC diseased tissue (FIGS. 9A–9D), the following methods and materials were employed:

Tissue Source: Histologically normal human tissues and tumors were obtained from surgical and autopsy specimens and prepared for immunohistochemical analysis (IMPATH, Los Angeles, Calif.). Fresh tissues were embedded in OCT compound (Miles Laboratories, Inc., Naperville, Ill.) and snap-frozen in isopentane cooled by liquid nitrogen. Specimens were stored at –80° C. until needed. Tissue was cut at 5 microns, placed on positively-charged slides, and air-dried. A human MM cell line (U266) served as a positive control, and two B cell lines (IM9, HT), were used as negative controls.

Reagents: The 51.2 MoAb was used as test antibody in the immunohistochemical analyses. The negative reagent control, murine IgG1, was purchased from DAKO Corporation (Carpinteria, Calif.). The antibodies were diluted to working concentrations with Primary Antibody Diluent (Research Genetics, Huntsville, Ala.).

Immunohistochemistry: Studies performed using an indirect peroxidase-conjugated immunohistochemical detection technique; the DAKO Envision+™ System (DAKO Corporation), according to the manufacturer's instructions. Cryostat-cut sections were removed from the –80° C. freezer, and air-dried for 30 minutes. Slides were fixed in acetone for 5 minutes at 4 C and washed in Phosphate Buffered Saline (PBS; Amresco, Solon, Ohio) at pH 7.2. Endogenous peroxidase activity was blocked with a 5-minute hydrogen peroxide solution, followed by PBS washes.

The slides were incubated with the 51.2 monoclonal antibody, or the isotype-matched control antibody, for 30 minutes at room temperature, followed by PBS washes. Next, the slides were incubated with an anti-mouse antibody conjugated to a peroxidase-labeled dextran polymer for 30 minutes at room temperature and then washed in PBS. The peroxidase reaction was visualized by incubating for 5±1 minutes with 3,3'-diaminobenzidine-tetrahydrochloride solution. The slides were thoroughly washed with tap water, counterstained with a modified Harris hematoxylin (American Master Tech. Scientific Inc., Lodi, Calif.), dipped in 0.25% acid alcohol, blued in 0.2% ammonia, dehydrated through graded alcohols, cleared in xylene, and coverslipped.

Controls: Positive control tissue sections were derived from a frozen cell block prepared from the U266 cell line. Negative control sections were derived from frozen cell blocks prepared from IM9 and HT cell lines. For the negative reagent control, the primary antibody was substituted with an isotype-matched control antibody at the same antibody concentration as the test article. The negative control section refers to the tissue section to which the isotype control antibody was applied.

Interpretation of Slides: Interpretation of stained slides was performed by microscopic examination. A morphologic review of the tissue on the slide determined whether an adequate amount of tissue was present, and whether the designated tissue was appropriately represented. Samples failing to meet the above standards were rejected from the analysis. The staining intensity of the test article was judged relative to the intensity of a control slide. Staining of the section labeled with the negative reagent control was considered "background."

Fixation Analyses: Analysis was performed using the positive and negative control cell lines, U266 and IM9, respectively. Of the fixatives evaluated (unfixed, acetone, ethanol, methanol/acetone, and 10% neutral buffered formalin), acetone for 5 minutes at 4° C. resulted in the best combination of morphological preservation and staining intensity.

The contents of all patent applications, issued patents, published articles and references, and textbooks as cited herein are hereby incorporated by reference in their entirety to more fully describe the state of the art to which the present invention pertains.

As various changes can be made in the above compositions and methods without departing from the scope and spirit of the invention, it is intended that all subject matter contained in the above description, shown in the accompanying drawings, or defined in the appended claims be interpreted as illustrative, and not in a limiting sense.

What is claimed is:

1. A monoclonal antibody or antigen binding fragment thereof which is produced by a hybridoma cell line deposited at the American Type Culture Collection (ATCC) having an ATCC Accession Number selected from the group consisting of ATTC Accession No. PTA-2360 (MoAb 51.2), ATCC Accession No. PTA-2358 (MoAb 37.14), ATCC Accession No. PTA-2357 (MoAb 109.12), and ATCC Accession No. PTA-2359 (MoAb 26.1).

2. A hybridoma cell line which is deposited at the American Type Culture Collection (ATCC) and having ATCC Accession Number selected from the group consisting of ATCC Accession No. PTA-2360 (MoAb 51.2), ATCC Accession No. PTA-2357 (MoAb 109.12), ATCC Accession No. PTA-2358 (MoAb 37.14), and ATCC Accession No. PTA-2359 (MoAb 26.1).

* * * * *